US008911744B2

(12) United States Patent
Kortekaas et al.

(10) Patent No.: US 8,911,744 B2
(45) Date of Patent: Dec. 16, 2014

(54) RECOMBINANT CLASSICAL SWINE FEVER VIRUS (CSFV) COMPRISING A MODIFIED E2 PROTEIN AND METHODS FOR GENERATING SAID RECOMBINANT CSFV

(75) Inventors: Jeroen Alexander Kortekaas, Zwolle (NL); Rianka Petronella Maria Vloet, Almere (NL)

(73) Assignee: Intervet International B.V., Boxmeer (NL)

( * ) Notice: Subject to any disclaimer, the term of this patent is extended or adjusted under 35 U.S.C. 154(b) by 593 days.

(21) Appl. No.: 13/141,182

(22) PCT Filed: Dec. 23, 2009

(86) PCT No.: PCT/NL2009/050801
§ 371 (c)(1),
(2), (4) Date: Aug. 11, 2011

(87) PCT Pub. No.: WO2010/074575
PCT Pub. Date: Jul. 1, 2010

(65) Prior Publication Data
US 2011/0287044 A1    Nov. 24, 2011

(30) Foreign Application Priority Data

Dec. 23, 2008   (EP) .................................... 08172874

(51) Int. Cl.
| | | |
|---|---|---|
| *C12N 7/01* | (2006.01) | |
| *A61P 31/14* | (2006.01) | |
| *C12Q 1/70* | (2006.01) | |
| *C07K 16/08* | (2006.01) | |
| *C12N 7/02* | (2006.01) | |
| *A61K 39/12* | (2006.01) | |
| *C07K 14/005* | (2006.01) | |
| *G01N 33/569* | (2006.01) | |
| *C12N 7/00* | (2006.01) | |

(52) U.S. Cl.
CPC ........ *C12N 7/00* (2013.01); *C12N 2770/24361* (2013.01); *C07K 14/005* (2013.01); *G01N 33/56983* (2013.01); *C12N 2770/24322* (2013.01)
USPC ...... 424/186.1; 424/218.1; 435/5; 435/235.1; 435/239; 530/387.9; 536/23.72

(58) Field of Classification Search
None
See application file for complete search history.

(56) References Cited

U.S. PATENT DOCUMENTS

| | | | |
|---|---|---|---|
| 5,149,527 A | 9/1992 | Weisenthal | |
| 6,180,109 B1 * | 1/2001 | Moormann et al. | ....... 424/204.1 |

(Continued)

FOREIGN PATENT DOCUMENTS

| | | |
|---|---|---|
| WO | 95/35380 A1 | 12/1995 |
| WO | WO00/53766 | 9/2000 |

(Continued)

OTHER PUBLICATIONS

Van Rijn et al. (Journal of General Virology. 1996; 77: 2737-2745).*

(Continued)

*Primary Examiner* — Shanon A Foley

(57) ABSTRACT

The invention relates to a recombinant classical swine fever virus (CSFV). A preferred recombinant CSFV comprises a deletion of at least one amino acid in a "TAVSPTTLR" domain of the E2 protein. The invention further relates to a vaccine comprising the recombinant CSFV, a method for generating a recombinant CSFV, and use of a recombinant CSFV.

16 Claims, 13 Drawing Sheets

SEQ ID NO.:65

(56) References Cited

U.S. PATENT DOCUMENTS

Figure 3:
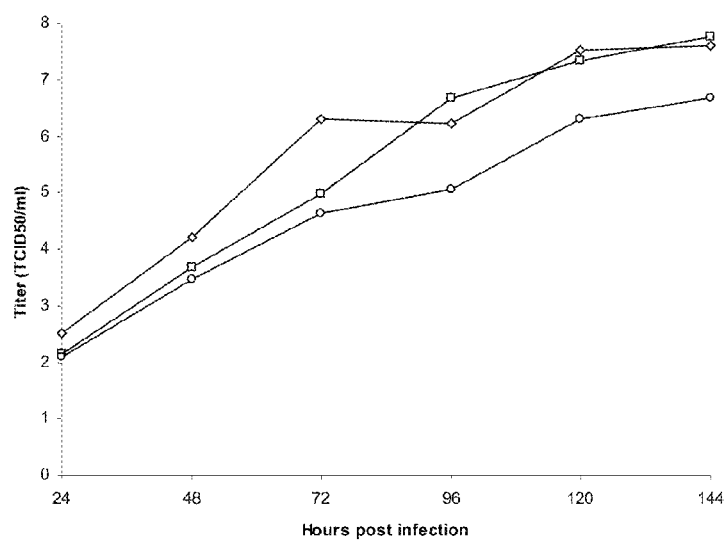
Figure 3:
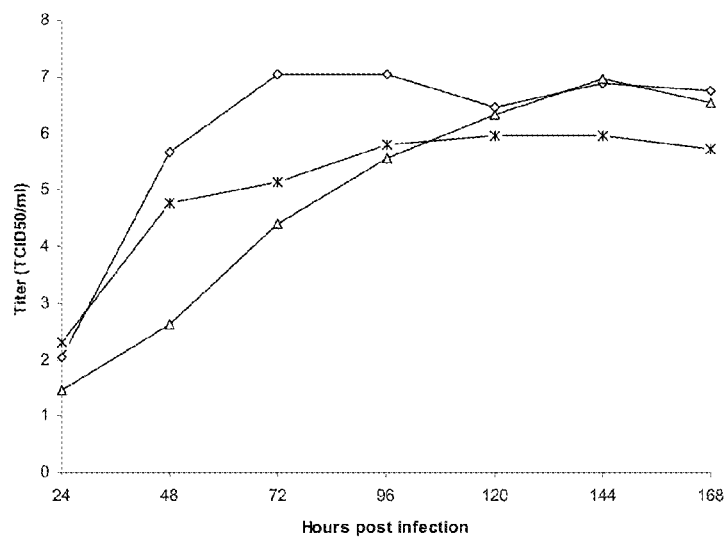

| | | | |
|---|---|---|---|
| 6,919,085 | B2 | 7/2005 | Kretzdorn et al. |
| 2005/0106153 | A1 | 5/2005 | Nordouist et al. |
| 2006/0177458 | A1 | 8/2006 | Kensil |
| 2007/0212328 | A1 | 9/2007 | Bruck et al. |
| 2007/0280955 | A1 | 12/2007 | Borca et al. |
| 2008/0292653 | A1* | 11/2008 | Borca et al. ............... 424/199.1 |
| 2011/0287044 | A1* | 11/2011 | Kortekaas et al. ......... 424/186.1 |

FOREIGN PATENT DOCUMENTS

| | | | |
|---|---|---|---|
| WO | WO2004/044220 | | 5/2004 |
| WO | WO 2007/143442 | * | 12/2007 |
| WO | WO2007/143442 | | 12/2007 |
| WO | WO2008/147799 | | 12/2008 |

OTHER PUBLICATIONS

Ruggli et al. (Journal of Virology. 1996; 70 (6): 3478-3487).*
Peng et al. (Virus Research. May 15, 2008; 135: 267-272).*
van Gennip et al. (Vaccine. 2001; 19: 447-459).*
Risatti et al. (Journal of Virology. 2007; 81 (2): 924-933).*
Frey, Caroline et al. "Classical Swine Fever Virus Replicon Particles Lacking the $E^{rns}$ Gene: A Potential Marker Vaccine for Intradermal Application", Veterinary Research, 37(5):655-670, Sep. 2006.
Kortekaas, J. et al. "Rational Design of a Classical Swine Fever C-Strain Vaccine Virus that Enables the Differentiation Between Infected and Vaccinated Animals", Journal of Virological Methods, 163(2):175-185, Sep. 2009.
Lin, Min et al., "Deletions of Structural Glycoprotein E2 of Classical Swine Fever Virus Strain Alfort/187 Resolve a Linear Epitope of Monoclonal Antibody WH303 and the Minimal N-Terminal Domain Essential for Binding Immunoglobulin G Antibodies of a Pig Hyperimmune Serum", Journal of Virology, The American Society for Microbiology, US, 74(24):11619-11625 , Dec. 2000.
Maurer, Roland, et al. "Oronasal Vaccination with Classical Swine Fever Virus (CSFV) Replicon Particles with Either Partial or Complete Deletion of the E2 Gene Induces Partial Protection Against Lethal Challenge With Highly Virulent CSFV", J. Vaccine, 23(25):3318-3328, May 2005.
Van Gennip, H.G.P.A, et al. "Experimental Non-Transmissible Marker Vaccines for Classical Swine Fever (CSF) by *Trans*-Complementation of $E^{rns}$ or E2 of CSFV", Vaccine, 20(11-12):1544-1556, Feb. 2002.
Van Rijn, P.A. et al. "An Experimental Marker Vaccine and Accompanying Serological Diagnostic Test Both Based on Envelope Glycoprotein E2 of Classical Swine Fever Virus (CSFV)", Vaccine, 17(5):433-440, Feb. 1999.
International Search Report for corresponding PCT/NL2009/050801, mailed Jun. 30, 2010.
Chavali et al., "An In Vitro Study of Immunomodulatory Effects of Some Saponins", Int. J. Immunopharmac., 1987, pp. 675-683, vol. 9(6).
Coulter et al., "Studies on Experimental Adjuvanted Influenza Vaccines: Comparison of Immune Stimulating Complexes (IscomsTM) and oil-in-water vaccines", Vaccine, 1998, pp. 1243-1253, vol. 16, No. 11/12.
Ferenbach et al., "Macrophages and dendritic cells: what is the difference?", Kidney International, 2008, pp. 5-7, vol. 74.
Francis et al., "The biological action of saponins in animal systems: a review", British Journal of Nutrition, 2002, pp. 587-605, vol. 88.
Lavelle, E., "Adjuvant Research", School of Biochemistry and Immunology, Trinity College Dublin, 2012, pp. 1-3, found at http://www.tcd.ie/Biochemistry/research/e_lavelle.php.
Muzzarelli, R., "Chitins and Chitosans as Immunoadjuvants and Non-Allergenic Drug Carriers", Marine Drugs, 2010, pp. 292-312, vol. 8.
Nature Reviews Immunology, Picture CD8/CD4 Relation, Jul. 29, 2013.
Van Gennip, et al., "Chimeric classical swine fever viruses containing envelope protein ERNS or E2 of bovine viral diarrhoea virus protect pigs against challenge with CSFV and induce a distinguishable antibody response", Vaccine, 2000, pp. 447-459, vol. 19, No. 4-5.

* cited by examiner

Fig. 1

|  | 772 | 823 | Fitness[d]: |
|---|---|---|---|
| vFlc34 (wildtype) | LFDGTNP STEEMGDDFRSGL // SEQ ID NO.:45 | TGVIEC TAVSPTTLR TEVVK SEQ ID NO.:46 | ++ |
| vFlc-N1 | ..................... | ............N......... | ++ |
| vFlc-N2 | ..................... | ............N..N...... | + |
| vFlc-N3 | ..................... | ..........N..N........ | † |
| vFlc-N4 | ..................... | ........N..N..N....... | † |
| vFlc-N5 | ..................... | ............NN........ | +[e] |
| vFlc-ΔP | ..................... | ............Δ......... | + |
| vFlc-ΔPT | ..................... | ............ΔΔ........ | † |
| vFlc-ΔSP | ..................... | ...........ΔΔ......... | † |
| vFlc-ΔSPT | ..................... | ...........ΔΔΔ........ | † |
| vFlc-ΔVSP | ..................... | ..........ΔΔΔ......... | † |
| vFlc-ΔAVSP | ..................... | .........ΔΔΔΔ......... | † |
| vFlc-ΔSPTTL | ..................... | ...........ΔΔΔΔΔ...... | – |
| vFlc-ΔPa1 | ................F.... | ............Δ......... | + |
| vFlc-ΔPTa1 | ..N.................. | ........G..ΔΔ......... | ++ |
| vFlc-ΔPTa2 | ..E.................. | ............ΔΔ........ | nd |
| vFlc-ΔPTa3, a5, a6, a7, a10, a11 | ..N.................. | ............ΔΔ........ | nd |
| vFlc-ΔPTa8 | ..................... | ...........E.ΔΔ....... | nd |

Fig. 2.

| vFlc34 | vFlc-N1 | vFlc-N2 |

| vFlc-ΔP | vFlc-ΔPTa1 |

A

B

A

B

C

Rabbit 1.1: vFlc34 (wildtype)

Rabbit 1.2: vFlc34 (wildtype)

Rabbit 2.1: vFlc-ΔPTa1

Rabbit 2.2: vFlc-ΔPTa1

Rabbit 2.3: vFlc-ΔPTa1

Fig. 7

SEQ ID NO.:65

A

B

C

A

B

RECOMBINANT CLASSICAL SWINE FEVER VIRUS (CSFV) COMPRISING A MODIFIED E2 PROTEIN AND METHODS FOR GENERATING SAID RECOMBINANT CSFV

CROSS-REFERENCE TO RELATED APPLICATIONS

This application is a national stage entry under 35 U.S.C. §371 of PCT/NL2009/050801 filed on Dec. 23, 2009, which claims priority to EP application No. 08172874.3 filed on Dec. 23, 2008. The content of PCT/NL2009/050801 is hereby incorporated by reference in its entirety.

The invention relates animal diseases. More specifically, the invention relates to a recombinant classical swine fever virus (CSFV) comprising a modified E2 protein. The invention further relates to a vaccine comprising said recombinant CSFV that allows differentiation of an infected animal from a vaccinated animal, and methods for generating said recombinant CSFV.

Classical swine fever virus (CSFV) is an enveloped, positive-strand RNA virus which, together with bovine viral diarrhoea virus (BVDV) and border disease virus (BDV), comprises the *Pestivirus* genus of the Flaviviridae family (Pringle, 1998. Arch Virol 143: 203-10). Introduction of CSFV in herds of domesticated pigs can result in huge economic losses (Terpstra and de Smit. 2000. Vet Microbiol 77: 3-15). Vaccination with a CSFV virus that has been attenuated by repeated passage in rabbits and cell culture, the so-called "Chinese" or "C"-strains, results in swift and livelong immunity against virulent CSFV. The C-strain virus is successfully used worldwide and is often referred to as the most effective veterinary vaccine ever produced. This vaccine, however, does not allow the serological differentiation between infected and vaccinated animals (DIVA). This is a major disadvantage, since the inability to detect CSF-infected animals in a vaccinated population can impose severe trade restrictions.

Diagnosis of CSF in the field can be performed by ELISAs that detect antibodies directed against either the structural glycoprotein $E^{rns}$ or E2. Several candidate vaccines have been developed that can fulfill the DIVA criterion when accompanied with the appropriate ELISA, varying from subunit vaccines (Hulst et al., 1993. J Virol 67: 5435-42) to live-attenuated viruses (van Gennip et al., 2000. Vaccine 19: 447-59; van Zijl et al., 1991. J Virol 65: 2761-2765) and replicon-based vaccines (van Gennip et al., 2002. Vaccine 20: 1544-56; Widjojoatmodjo et al., 2000. J Virol 74: 2973-2980).

The commercially available DIVA vaccine against CSF is based on baculovirus-produced E2, which is accompanied by a serological test that detects antibodies directed against $E^{rns}$ (Van Aarle, 2003. Dev Biol Stand Basel 114: 193-200). Although this vaccine provides protection against CSF, it is less efficacious than the C-strain vaccine with respect to both the onset and duration of immunity (van Oirschot, 2003. Vet Microbiol 96: 367-84). More importantly, $E^{rns}$ ELISAs that accompany this vaccine, also detect other members of the *pestivirus* genus (i.e. BVDV and BDV). Their use is, therefore, not recommended in regions were these viruses circulate (2003/265/EC; SANCO/10809/2003).

Furthermore, the sensitivity of $E^{rns}$ ELISAs was previously found to be insufficient to diagnose individual animals and should therefore only be used on a herd basis with sufficiently large numbers of animals (Blome et al., 2006. Rev Sci Tech 25: 1025-38; Floegel-Niesmann, 2003. Dev Biol (114: 185-91). This explains why, in general, E2 ELISAs are greatly preferred over $E^{rns}$ ELISAs in accompanying a DIVA vaccine.

The E2 protein contains two major antigenic domains, namely the B/C domain and the A domain (van Rijn et al., 1993. J Gen Virol 74: 2053-60; Wensvoort, 1989. J Gen Virol 70: 2865-76). Domain A, which is located between amino acids 766 and 866 of the CSFV polyprotein, is divided in subdomains A1, A2 and A3 (Wensvoort, 1989. J Gen Virol 70: 2865-76). Despite the fact that the A1 domain is a dominant target for neutralizing antibodies, it has been conserved throughout evolution. In fact, its sequence conservation and immunodominance have rendered it the dominant target in E2 ELISAs.

Although outbreaks of CSF are currently controlled by quarantine restrictions and slaughtering of suspected herds, there is an urgent need for the implementation of more humane and more economical intervention strategies to control future CSF outbreaks. Therefore, there is an urgent need for a DIVA vaccine that is accompanied by a robust and CSFV-specific ELISA.

The present invention provides a recombinant classical swine fever virus (CSFV), comprising a deletion of at least one amino acid in the "TAVSPTTLR (SEQ ID NO.:1" domain of the E2 protein, corresponding to position 829 to 837 of a parental CSFV polyprotein.

With polyprotein is meant the about 4000 amino acid hypothetical polyprotein that is formed upon translation of the viral RNA. Said polyprotein is processed to form the final cleavage products $N^{pro}$-C-Erns-E1-E2-p7-N52-N53-NS4A-NS4B-NS5A-NS5B.

The CSFV E2 protein contains a recently identified epitope that comprises the amino acid sequence TAVSPTTLR (SEQ ID NO.:1) (residues 829-837 of the CSFV polyprotein; using single letter code for amino acids) (Lin et al., 2000. J Virol 74: 11619-25). This epitope shares all characteristic features of the A1 domain, being immunodominant, evolutionarily conserved, specific for CSFV and a target for neutralizing antibodies. A comparison of the sequences around the TAVSPTTLR (SEQ ID NO.:1) domain among E2 proteins from different strains of pestiviruses indicates that the sequence TAVSPTTLR (SEQ ID NO.:1) is strongly conserved among strains of CSFV and is highly variable among strains of BVDV and BDV (Lin et al., 2000. J Virol 74: 11619-25).

Antibodies, especially monoclonal antibodies, used in E2-specific ELISAs that recognize the TAVSPTTLR (SEQ ID NO.:1) domain do not cross react with other members of the pestivirus genus and can therefore be used in regions were these other viruses circulate. Said antibodies will not recognize a recombinant CSFV according to the invention, comprising a deletion in said domain of the E2 protein.

Thus, said recombinant virus enables to differentiate animals that are infected with the recombinant virus from animals that are infected with wild-type CSFV and from animals that are not infected and/or that are not vaccinated. Furthermore, the use of said recombinant virus will allow the use of a peptide-based diagnostic test to discriminate between these animals.

The present invention provides a recombinant classical swine fever virus (CSFV), comprising a deletion of at least one amino acid in the "TAVSPTTLR (SEQ ID NO.:1)" domain of the CSFV, or an equivalent thereof. An equivalent domain is a domain within the E2 region in which one amino acid is substituted for another amino acid, such as an amino acid that belongs to the same group, i.e. an aromatic amino acid that is replace by another aromatic amino acid, or an aliphatic amino acid that is replace by another aliphatic amino acid.

Said parental genome preferably comprises a substantially complete viral genome derived from a CSFV strain, preferably a naturally occurring or recombinant attenuated CSFV strain. The term parental genome comprises a nucleic acid molecule, such as a RNA molecule and/or a cDNA copy thereof.

With the term "deletion of at least one amino acid", as used in the description, is meant the removal of at least one amino acid. The term "deletion" does not cover a removal of at least one amino acid, followed by insertion of another at least one amino acid at the same position. Therefore, the term "deletion" as used herein does not cover the substitution of an amino acid for another amino acid.

Said recombinant cDNA molecule preferably comprises a substantially complete recombinant classical swine fever virus (CSFV) genome, whereby said genome encodes an E2 protein that comprises a deletion of at least one amino acid in the conserved "TAVSPTTLR (SEQ ID NO.:1)" domain corresponding to position 829 to 837 of the CSFV polyprotein. The term "substantially complete" indicates that said a virus generated by said genome is able to infect a suitable cell or cell line, and can be reproduced in said suitable cell or cell line. A "substantially complete" viral genome preferably is a replication-competent genome. More preferred is an infectious, replication-competent and packaging-competent viral genome. It is furthermore preferred that also the recombinant classical swine fever virus (CSFV) comprises a "substantially complete" viral genome, preferably a replication-competent genome, or, more preferred, an infectious, replication-competent and packaging-competent viral genome.

In a preferred embodiment, a deletion of at least one amino acid in the TAVSPTTLR (SEQ ID NO.:1) domain of a recombinant CSFV according to the invention comprises a deletion of the central proline of said "TAVSPTTLR (SEQ ID NO.:1)" domain.

Proline is unique among the 20 common amino acids in having the side-chain cyclized onto the backbone nitrogen atom. This restricts the conformation of said praline and also of the residue preceding the proline. Furthermore, proline can act as a conformational 'switch', allowing parts of proteins to adopt alternative conformations, Alteration of the central proline in the TAVSPTTLR (SEQ ID NO.:1) domain, therefore, not only changes the primary sequence, but also changes the conformation of the immunogenic TAVSPTTLR (SEQ ID NO.:1) domain. An E2 protein that comprises a deletion of the central proline of the TAVSPTTLR (SEQ ID NO.:1) domain will not be recognized by antibodies that recognize said domain within the E2 protein.

In a further preferred embodiment, an altered E2 protein of a recombinant CSFV according to the invention comprises a deletion of at least two amino acids From said TAVSPTTLR (SEQ ID NO.:1) domain. A deletion of two amino acids comprises deletion of TA, AV, VS, SP, PT, TT, TL and LR, respectively, from the TAVSPTTLR (SEQ ID NO.:1) domain of E2, A most preferred deletion of two amino adds is a deletion of PT at position 833-834 in the TAVSPTTLR (SEQ ID NO.:1) domain.

In a further preferred embodiment, an altered E2 protein of a recombinant CSFV according to the invention comprises a deletion of at least three amino acids from said TAVSPTTLR (SEQ ID NO.:1) domain, such as three amino acids, four amino acids, five amino adds, six amino adds, seven amino adds, eight amino adds or nine amino adds. A further preferred E2 protein comprises a deletion of the amino add sequences VSP, SPT, AVSP, or SPTTL.

The invention further provides a recombinant CSFV according to the invention, comprising at least one further alteration of the parental CSFV genome. Viruses comprising a deletion in said conserved TAVSPTTLR (SEQ ID NO.:1) domain were less efficient in infecting cells, compared to the parental virus, and/or were less efficiently replicated in infected cells, resulting in a lower titer as compared to the parental virus. Continued passaging of cells infected with a virus comprising a deletion in the conserved TAVSPTTLR (SEQ ID NO.:1) domain resulted in a rescued virus that more efficiently infected and/or replicated in cells, resulting in titers that were comparable to titers of the parental virus. The rescued virus had introduced one or more further alterations in the parental genome that compensated for the loss of fitness of the virus with a deletion in the conserved TAVSPTTLR (SEQ ID NO.:1) domain.

In one embodiment, said at least one further alteration is a silent mutation that changes the genome of the virus but does not result in an alteration of an amino acid. Said silent mutation is present in a non-coding part of the viral genome, or a coding part of the viral genome, such as in a part of the viral genome encoding $N^{pro}$, C, $E^{rns}$, E1, and/or E2, and/or in a part encoding non-structural proteins. A silent mutation may contribute to the fitness recovery of the altered viruses at some point during the generation of these viruses. Without being bound by theory, a silent mutation, for example, results in an improved stability of the viral genome and/or an improved replication because said silent mutation alters a conformation of the viral genomic nucleic acid. Furthermore, said silent mutation may result in improved codon usage. A preferred silent mutation is provided by a U to C alteration at position 1549 in the $E^{RNS}$ gene.

In a further embodiment, said at least one further alteration is in a region encoding the E1 protein which is known to assemble into disulphide-linked heterodimers with the E2 protein. A deletion in the conserved TAVSPTTLR (SEQ ID NO.:1) domain of E2 is thus, at least partially, compensated by an alteration of at least one amino acid in the E1 protein. In a further embodiment, said at least one further alteration is in a region encoding the $N^{pro}$, C, $E^{rns}$ or E2 protein. Said at least one further alteration preferably comprises at least two alterations in different regions selected from the regions encoding the $N^{pro}$, C, $E^{rns}$, E1, and/or E2 protein, or within one region encoding the $N^{pro}$, C, $E^{rns}$, E1, and/or E2 protein. Said at least two further alterations preferably comprise at least one silent mutation. A preferred silent mutation is provided by a U to C alteration at position 1549 in the $E^{RNS}$ gene.

In a preferred embodiment, said at least one further alteration results in the introduction of an additional N-linked glycosylation site in the E2 protein An N-linked glycosylation site at an additional position in the E2 protein apparently compensates, either directly or by virtue of its function as an anchor site for a carbohydrate moiety, for the loss of fitness imposed by said deletion in the TAVSPTTLR (SEQ ID NO.:1) epitope. In a preferred embodiment, said N-linked glycosylation site is introduced by alteration of the LFDGTNP (SEQ ID NO.:5) domain from amino acid position 772-778, such as, for example, an alteration of D to N at position 774. Alternatively, or in addition, an N-linked glycosylation site is introduced by alteration of A to N at position 830 in the E2 protein.

Said further alteration preferably alters a codon at positions 1547-1549, encoding V392 within the $E^{rns}$ protein; a codon at positions 2273-2275, encoding E634 within the E1 protein; a codon at positions at position 2693-2695 encoding D774 within the E2 protein; and/or a codon at positions at position 2864-2866 encoding V831 within the E2 protein. Said alteration of a codon at the indicated positions comprises either a silent mutation, or comprises an alteration of the encoded amino acid. A preferred at least one further alteration comprises a substitution of valine (V) at position 831 for glycine (G).

In another preferred embodiment, said at least one further alteration of the parental genome results in a substitution of S to F at position 789 and/or a substitution of A to T at position 445. The serine at position 789 and the alanine at position 445 are present in all C-strain viruses and related lapinized CSFV strains, whereas phenylalanine at position 789 and threonine at position 445 are conserved in virulent CSFV strains. Although the history of the C-strain virus is not well documented, it is clear that the virus was attenuated by passage in rabbits hundreds of times, for which an S at position 789 and an A at position 445 may be beneficial. The alteration of S to F at position 789 and the alteration of A to T at position 445 are likely beneficial for propagation of a virus comprising a deletion in the TAVSPTTLR (SEQ ID NO.:1) epitope, whereas it will be dose to neutral in a virus comprising the TAVSPTTLR (SEQ ID NO.:1) epitope.

In yet a further preferred embodiment, the invention provides a recombinant CSFV comprising a deletion of P at position 833 and a silent alteration. A preferred silent alteration is a U to C alteration at position 1549 in the $E^{RNS}$ gene. A further preferred recombinant CSFV comprises a deletion of P at position 833 and an alteration of S to F at position 789 and/or an alteration of A to T at position 445; a deletion of P at position 833, an alteration of D to N at position 774, a substitution of V to G at position 831, and a deletion of T at position 834, either or not in addition to a U to C alteration at position 1549. A most preferred recombinant CSFV comprises a deletion of proline and threonine at position 833 and 834, respectively, of the "TAVSPTTLR (SEQ ID NO.:1)" domain of the E2 protein, a U to C alteration at position 1549, a substitution of a glutamic acid (E) for aspartic acid (D) at position 634, a substitution of aspartic acid (D) for asparagine (N) at position 774 in the E2 protein, and a substitution of valine (V) for glycine (G) at position 831.

In a further embodiment, the invention provides a recombinant classical swine fever virus (CSFV), comprising an alteration of at least one amino acid in a "TAVSPTTLR (SEQ ID NO.:1)" domain from position 829 to 837 in E2 of a parental CSFV polyprotein, whereby said alteration comprises a substitution of the central proline in the TAVSPTTLR (SEQ ID NO.:1) domain to asparagine. Said substitution was found to minimize or even inhibit binding of E2-specific monoclonal antibodies to the altered E2 protein.

Apart from changing the primary amino acid sequence, the introduction of said asparagine results in the introduction of an N-linked glycosylation site comprising the glycosylation consensus sequence [N-x-S/T], wherein x denotes any amino acid except for P or D (Kornfeld and Kornfeld, 1985. Annu Rev Biochem 54: 631-64). N-glycosylation of viral proteins has been implicated in immunogenicity, whereby the introduction of an N-linked glycosylation can limit both cellular and antibody response to a viral protein. Said substitution can thus be used to generate a recombinant virus that allows differentiation of animals infected with a wild type virus from animals infected with said recombinant virus.

In one embodiment, a recombinant CSFV, comprising a substitution of the central proline in the TAVSPTTLR (SEQ ID NO.:1) domain to asparagine, comprises at least one further alteration in the genome. A preferred at least one further alteration results in an additional N-glycosylation site in $N^{pro}$, C, $E^{rns}$, E1, and/or E2, and/or in a part encoding non-structural proteins. A preferred additional N-glycosylation is present within E2, such as, for example, within the TAVSPT-TLR (SEQ ID NO.:1) domain or within a LFDGTNP (SEQ ID NO.:5) epitope of the E2 protein.

A further preferred at least one further alteration is a silent mutation present in a non-coding part of the viral genome, or in a coding part of the viral genome, such as in a part of the viral genome encoding $N^{pro}$, C, $E^{rns}$, E1, and/or E2, and/or in a part encoding non-structural proteins. A preferred silent mutation is provided by a U to C alteration at position 1549 in the $E^{RNS}$ gene.

Yet a further preferred at least one further alteration comprises an alteration of at least one amino add in $N^{pro}$, C, $E^{rns}$, E1, end/or E2, and/or in a part encoding non-structural proteins. Said at least one further alteration is preferably selected from a silent alteration, for example a U to C alteration at position 1549 in the $E^{RNS}$ gene, a alteration of S to F at position 789, an alteration of A to T at position 445, an alteration of D to N at position 774, an alteration of V to G at position 831, and/or a deletion of T at position 834. R is even more preferred that said at least one further alteration comprises at least two further alterations, selected from a silent mutation, an additional N-glycosylation site, and/or an amino acid alteration, in addition to substitution of the central proline in the TAVSPTTLR (SEQ ID NO.:1) domain to asparagine. Said at least two further alterations are present in the same protein or in different proteins selected from $N^{pro}$, C, $E^{rns}$, E1, E2, and non-structural protein. It is preferred that said at least two further alterations are present in the same protein or in different proteins selected from $N^{pro}$, C, $E^{rns}$, E1, and E2.

In yet a further embodiment, the invention provides a recombinant classical swine fever virus (CSFV), comprising an addition of at least one amino acid in a "TAVSPTTLR (SEQ ID NO.:1)" domain from position 829 to 837 in E2 encoded by a parental CSFV genome. Said insertion addition will minimize or even inhibit binding of E2-specific monoclonal antibodies to the altered E2 protein. An insertion of at least one amino acid in a "TAVSPTTLR (SEQ ID NO.:1)" domain is preferably combined with at least one further alteration selected from a silent mutation, an additional N-glycosylation site, and/or an amino acid alteration, of a combination thereof, in $N^{pro}$, C, $E^{rns}$, E1, E2, and non-structural protein. Said at least one further alteration is preferably selected from a silent alteration, for example a U to C alteration at position 1549 in the $E^{RNS}$ gene, an alteration of S to F at position 789, an alteration of A to T at position 445, an alteration of D to N at position 774, and/or an alteration of V to G at position 831

The parental genome of a recombinant CSFV according to the invention preferably is the genome of an attenuated CSFV strain.

Attenuated CSFV strains can be generated by mutation of the $E^{rns}$ gene encoding a protein with RNase activity (Mayer et al., 2003. Virus Res. 98: 105-16); by deletion of $N^{pro}$ from CSFV virulent strains (Mayer et al. 2004. Vaccine 22: 31.7-328); by combining mutations in $E^{rns}$, and E2 (van Gennip et al. 2004. J. Virol. 78: 8812-8823); by mutation of the E1 gene (Risatti et al. 2005. Virology 343: 116-127); and by mutation of the E2 gene (Risatti et al., 2007. Virology 364: 371-82).

A preferred attenuated CSFV strain comprises an insertion in the 3' terminal non-coding region. For example, an insertion of 12 nucleotides in the 3 untranslated region leads to attenuation of CSFV (Wang et al., 2008. Virology 374: 390-8). Said insertion preferably comprises a sequence of 12 nucleotides consisting of 5'-CUUUUUUCUUUU (SEQ ID NO.:4).

A most preferred parental genome is the genome of C (Chinese)-strain. Even more preferred as a parental genome is the genome of the Cedipest C-strain, which is a C-strain virus that was adapted to suspension cultures of the swine kidney cell line SK6 (Terpstra et al., 1990. Dtsch Tierarztl Wochenschr. 97:77-9). Pigs inoculated with 400-600 TCID50 of the Cedipest strain are fully protected against challenge with greater than 100 pig LD50 of a virulent strain of CSFV at 7 days and at 6 month post vaccination. Therefore, the invention also provides a cDNA molecule comprising a copy of a recombinant classical swine fever virus (CSFV) genome encoding an altered "TAVSPTTLR (SEQ ID NO.:1)" domain from position 829 to 837 in E2. Said cDNA molecule preferably comprises a substantially complete recombinant parental CSFV viral genome according to the invention, whereby said parental genome is derived from the C (Chinese)-strain, or, more preferred, from the Cedipest strain. A preferred cDNA molecule comprises a copy of a recombinant CSFV genome encoding an E2 protein comprising a deletion of at least one amino acid in a "TAVSPTTLR (SEQ ID NO.:1)" domain. The invention also provides an antibody, preferably a monoclonal antibody, that specifically recognizes said altered "TAVSPTTLR (SEQ ID NO.:1)" domain. The invention further relates to a construct encoding a protein comprising said altered, "TAVSPTTLR (SEQ ID NO.:1)" domain. The invention further relates to a protein comprising said altered, "TAVSPTTLR (SEQ ID NO.:1)" domain, and to a peptide comprising said altered, "TAVSPTTLR (SEQ ID NO.:1)" domain, and to the use of said protein or peptide in an immuno-assay such as, for example, an ELISA.

In a further aspect, the invention provides a live CSF vaccine comprising a recombinant CSFV according to the invention.

A vaccine, or immuno active composition, comprising a recombinant CSFV according to the invention combines the rapid induction and length of protection induced by a live, attenuated virus with the possibility of differentiating between vaccinated animals and animals that are infected with wild type virus due to a difference, such as a deletion, in the conserved TAVSPTTLR (SEQ ID NO.:1) domain of E2, which is an important immunodominant epitope of the E2 protein.

Several vaccines have been developed that lead to a marked reduction in the levels of circulating virus and a concomitant reduction of clinical cases. For example, a subunit vaccine against CSFV has been developed that is based on the envelope glycoprotein E2. This subunit vaccine allows discrimination between vaccinated and infected pigs on the basis of the detection of antibodies against $E^{RNS}$ K (Van Aarle, 2003. Dev Biol Stand (Basel) 114: 193-200). However, the vaccine is inferior to the C-strain vaccine with respect to both the onset and duration of immunity. More importantly. $E^{rns}$ ELISAs that accompany this vaccine, also detect other members of the *pestivirus* genus (i.e. BVDV and BDV). Their use is, therefore, not recommended in regions were these viruses circulate (2003/265/EC; SANCO/10809/2003).

A further vaccine is provided by a so-called virus replicon particle (VRP). A VRP particle contains a mutant genomic RNA which is able to replicate and to express the encoded viral proteins but which does not contain the complete information required for particle formation due to deletions in at least one of the genes encoding a viral structural protein. These virus particles are non-transmissible and, therefore, fulfill one of the requirements for a safe vaccine. However, VRP with a partial or complete deletion of the E2 gene induced only partial protection against lethal challenge with highly virulent CSFV (Maurer et al., 2005. Vaccine 23: 3318-28).

The invention further provides a method of protecting an animal against CSF, comprising administering to said animal an effective amount of a vaccine according to the invention.

An effective amount is defined as an amount of said vaccine that will induce an immunological response in the individual to which it is administered resulting in the development in the individual of a secretory, cellular and/or antibody-mediated immune response to the vaccine. Said secretory, cellular and/or antibody-mediated immune response to the vaccine is also effective against a challenge with a virulent CSFV strain.

Said effective amount is preferably administered orally or oronasally or intramuscularly. An immunogenic composition against classical swine fever, comprising a recombinant CSFV according to the invention, is preferably administered together with a pharmaceutically acceptable carrier.

A further method of protecting an animal against CSF comprises the provision an effective amount of a vaccine according to the invention as a bait vaccine, especially to protect wild animals such as wild boars.

Efficacious vaccines reduce or prevent clinical signs by preventing virus replication and/or reducing virus transmission. The term DIVA (differentiating infected from vaccinated, animals) is used for vaccines and their companion diagnostic tests which are based on mutants of wild-type viruses, in conjunction with a differentiating diagnostic test. This system makes possible the mass vaccination of a susceptible animal population without compromising the serological identification of convalescent animals.

The invention furthermore provides a method of differentiating animals infected with CSFV from non-infected animals or from animals vaccinated with the CSF vaccine according to the invention, comprising analyzing serum of an animal in a serological test. It is preferred that said CSFV vaccine comprises an alteration of the TAVSPTTLR (SEQ ID NO.:1) domain according to the invention, and, more preferred, at least one further alteration in the E2 protein such as, for example, an alteration in LFDGTNP (SEQ ID NO.:5) domain from amino add position 772-778.

Said serological test preferably comprises one or more antibodies such as monoclonal antibodies that recognize an E2 protein comprising an intact TAVSPTTLR (SEQ ID NO.: 1) domain, and one or more antibodies such as monoclonal antibodies that recognize a further epitope encoded by CSFV, such as a further epitope within the E2 protein for example the LFDGTNP (SEQ ID NO.:5) epitope.

Ina preferred embodiment, said antibody enzyme-linked immunosorbent assays (ELISAs) allow diagnosis of CSF in live pigs. Preferred ELISAs are sandwich type ELISAs. A preferred ELISA is a competition ELISA based on E2, such as, for example, Ceditest 2.0 ELISA. By pre-incubating serum of an animal with a mutant E2 protein comprising an altered TAVSPTTLR (SEQ ID NO.:1) domain, either or not in combination with an altered LFDGTNP (SEQ ID NO.:5) domain, it is possible to deplete said serum for antibodies that are directed against said altered TAVSPTTLR (SEQ ID NO.: 1) domain and altered LFDGTNP (SEQ ID NO.:5) domain.

A most preferred ELISA is a peptide-based ELISA, wherein peptides are cross-linked to micro-well assay plates. Said cross-linking preferably is performed through an anchor protein such as, for example, poly-L-lysine. ELISAs employing cross-linked peptides are in general more sensitive when compared to ELISAs employing passively coated peptides. The technique is relatively simple to perform, does not require tissue culture facilities, is suitable for automation and can provide results within half a day. Monoclonal and/or polyclonal antibodies can be used that unambiguous differentiate between field and vaccine strains of CSFV on the one hand, and between CSFV and other pestiviruses on the other, peptide) could be used to block unspecific cross-reactivity.

Said peptide-based ELISA preferably is a liquid-phase peptide ELISA (lp-ELISA). In said lp-ELISA for detection of antibodies against CSFV, a test serum is incubated with a mixture of a modified CSFV peptide and a heterologous control peptide, for example a BVDV peptide. Said modified CSFV peptide is preferably biotinylated, while the control peptide is not biotinylated. CSFV-specific antibodies will bind to said CSFV peptide and are captured by through said modification, for example by binding to avidin or streptavidin of the CSFV peptide is biotinylated. Antibodies that are complexed to the modified CSFV peptide can be detected, for example complexed swine antibodies are detected by an anti swine-peroxidase conjugate and subsequent incubation with a suitable substrate.

An alternative test for the differentiation of an animal that is infected with field CSFV or vaccinated with a recombinant virus of the invention is provided by a fluorescent antibody test (FAT) and reverse transcriptase followed by amplification of the cDNA, for example by the polymerase chain reaction, and analysis of the sequence of the amplified. DNA. FAT is used to detect CSFV antigen in cryostat sections of tonsils, spleen, kidney, lymph nodes or distal portions of the ileum isolated from a pig that is suspected to be infected with CSFV or that is vaccinated with a vaccine according to the invention. In an alternative test, CSFV is isolated from, for example, the tonsils of an animal that is infected or suspected to be infected with field CSFV and incubated with PK-15 cells. Replicated virus is subsequently detected in the PK-15 cells using antibodies that differentiate between a field virus and a recombinant virus according to the invention.

A further preferred serological test comprises a competitive ELBA to determine if said serum comprises antibodies that inhibit binding of an antibody directed against an E2 protein comprising an intact TAVSPTTLR (SEQ ID NO.:1) domain, or if said serum comprises antibodies that inhibit binding of an antibody directed against an E2 protein comprising an altered TAVSPTTLR (SEQ ID NO.:1) domain.

Yet a further preferred serological test comprises one or more antibodies, preferably monoclonal antibodies, which specifically recognize an E2 protein comprising an altered TAVSPTTLR (SEQ ID NO.:1) domain according to the invention. In an even more preferred embodiment, said serological test comprises one or more antibodies such as monoclonal antibodies that specifically recognize an E2 protein comprising an altered TAVSPTTLR (SEQ ID NO.:1) domain according to the invention and a further altered immunogenic domain of said E2 protein. Said marker vaccine requires the reliable induction and detection (sensitive and specific) of discriminatory antibodies after vaccination of animals. The presence of said discriminatory antibodies is detected by said serological test which is preferably selected from a fluorescent antibody virus neutralization test, a neutralizing peroxidase-linked assay, and an antibody ELISA.

The invention further provides a method for isolating an infectious recombinant virus that can be used in a marker vaccine which allows differentiating infected animals from vaccinated animals, the method comprising selecting an immuno-dominant domain of a protein encoded by said virus and which is conserved in at least 90% of the viruses, preferably in at least 95% of the viruses, more preferred in at least 99%, of the viruses; introducing an alteration, preferably a deletion, in a genome region of said virus that encodes said immunodominant domain such as to generate a starting virus; contacting the altered genome with a suitable cell or cell line; passaging the suitable cell or cell line to allow propagation of a virus; and isolating an infectious virus from said suitable cell or cell line which comprises one or more further alterations in the genome that compensate a loss of fitness of the starting virus.

Said alteration in a conserved, immuno-dominant domain of a protein allows the generation of antibodies, such as monoclonal and polyclonal antibodies, that discriminate a virus that expresses a wild type immuno-dominant domain from a virus that expresses an altered immuno-dominant domain. Therefore, the invention also provides an antibody, preferably a monoclonal antibody, that specifically recognizes said altered, conserved, immuno-dominant domain.

The invention further relates to a construct encoding a protein comprising said altered, conserved, immuno-dominant domain. The invention further relates to a protein comprising said altered, conserved, immuno-dominant domain, and to a peptide comprising said altered, conserved, immuno-dominant domain.

A vaccine comprising an alteration in a conserved, immuno-dominant domain furthermore does not induce the generation of antibodies in a vaccinated individual that recognize an unaltered immuno-dominant domain, A diagnostic test directed at recognizing said unaltered conserved, immuno-dominant domain allows to discriminate an animal infected with a virus that expresses a wild type immuno-dominant domain from a vaccinated animal.

Said alteration of a conserved, immuno-dominant domain may result in a virus that is less efficient in infecting cells, compared to the wild type virus, and/or that is less efficiently replicated in infected cells. Passaging of an infected cell or cell line enables the introduction of one or more second site genomic alterations that rescue the virus. Said rescued virus more efficiently infects and/or replicates in cells, compared to the altered virus, or has antagonized another disadvantage that correlates with the alteration of a conserved, immuno-dominant domain. The rescued virus therefore comprises one or more further alterations in the parental genome that compensate for a loss of fitness introduced by the alteration in a conserved, immuno-dominant domain. A further advantage of a method according to the invention is that the additional one or more further alterations in the parental genome will hamper the generation of a revertant virus comprising a parental immuno-dominant domain.

In a preferred method according to the invention, said alteration in a genome region results in a deletion of at least one amino acid. A deletion of at least one amino acid, such as one amino acid, two amino acids, three amino acids or more than three amino acids, will further hamper the generation of a revertant virus comprising a parental immuno-dominant domain.

In a further preferred method according to the invention, a deletion of at least one amino acid is combined with at least one further alteration in the genome of the parental virus. Said at least one further alteration allows the passaging of an infected cell or cell line of the starting virus in the event said deletion of at least one amino acid is detrimental for replication of the virus in said cell or cell line. The introduction of said at least one further alteration restores fitness of the starting virus to some extent, allowing the starting virus to replication in said cell or cell line.

In a preferred embodiment, said virus is selected from negative stranded RNA viruses, such as rabies virus and Newcastle Disease Virus, and positive stranded RNA viruses such as Flaviviridae, preferably a *pestivirus* such as bovine viral diarrhoea virus, border disease virus, and CSFV. A most preferred virus for a method of the invention is CSFV.

The invention further provides an infectious recombinant virus, preferably CSFV, obtainable by the method of the invention.

The invention also provides the use of an infectious recombinant virus, preferably CSFV, obtainable by the method of the invention, such as the use in a vaccine for vaccinating one or more animals to protect said animal against infection with a virulent field virus.

Said use of the vaccine allows differentiating infected animals from not infected animals or vaccinated animals.

A major advantage of an efficacious marker vaccine is that it allows the detection of infected pigs in a vaccinated pig population, and thus offers the possibility to monitor the spread or re-introduction of CSFV in a pig population. Thus, it makes it possible to declare, with a certain level of confidence, that a vaccinated pig population is free of CSF on the basis of laboratory test results.

The latter could result in a shortening of the restriction period for the export of live pigs or pig products. The economic advantage of a rapid resumption of trade is obvious and therefore closely related to the use of any marker vaccine.

FIGURE LEGENDS

FIG. 1. Introduced and adaptive mutations in E2.

$^a$Comparison of the amino acids from positions 772 to 791 (SEQ ID NO: 45) and 823 to 842 (SEQ ID NO: 46) of the recombinant viruses under study.

$^b$Introduced amino acid substitutions are indicated in bold, adaptive mutations are indicated in bold italics.

$^c$The TAVSPTTLR (SEQ ID NO.:1) and LFDGTNP (SEQ ID NO.:5) epitopes are boxed.

$^d$++; Virus was rescued and growth was comparable to that of vFlc34 (wildtype), +; Virus with impaired growth compared to vFlc34, †; Virus was lost from the culture medium after a few passages, –; No virus was detected, nd; Not determined.

$^e$One of the newly introduced AAU codons was deleted during propagation of the virus.

Figure 2:
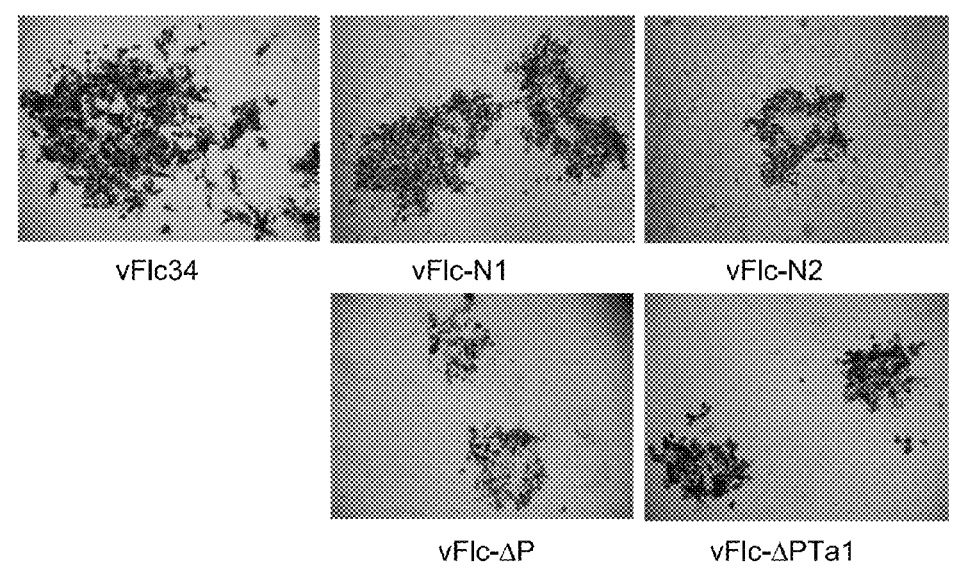

FIG. 2. In vitro growth characteristics of vFlc34 (wildtype C-strain), C-strain glycosylation mutations vFlc-N1 and vFlc-N2 and C-strain deletion mutants vFlc-ΔP and vFlc-ΔPTa1. SK6.T7 monolayers were infected, covered with growth medium containing methylcellulose and incubated at 37° C. for four days. Monolayers were fixed with 4% paraformaldehyde and immunostained with peroxidase-conjugated mAb WB103.

FIG. 3. (A) Multistep growth curves of viruses vFlc34 (◇), vFlc-N1 (□), vFlc-N2 (○), and (B) of vFlc34 (◇), vFlc-ΔP (x) and vFlc-ΔPTa1 (Δ). SK6.T7 cells were infected with a multiplicity of infection of 0.1.

Figure 4:
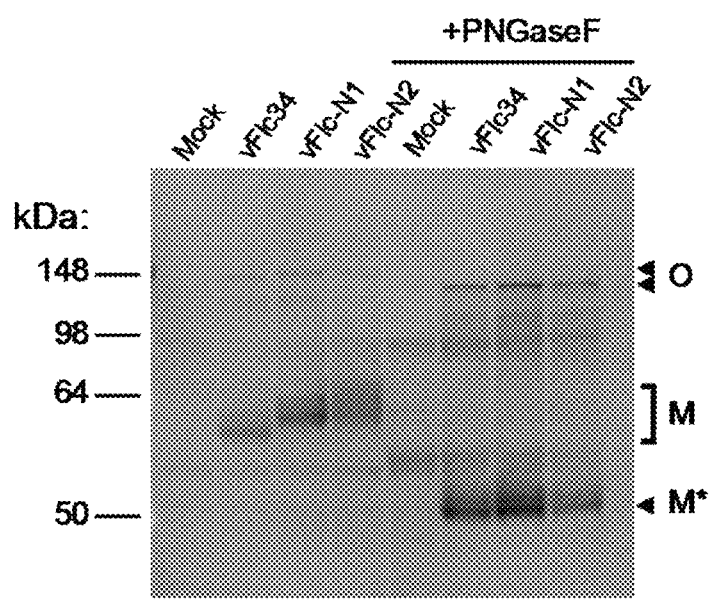

FIG. 4. Western blot of a denaturing PAGE gel containing lysates of SK6.T7 cells non-infected (mock), or infected with vFlc34, vFlc-N1 or vFlc-N2, respectively, and the same samples after treatment with PNGase F. Proteins were detected by mAb C2 and peroxidase-conjugated rabbit anti-mouse immunoglobulins as the secondary antibody. The positions of oligomers (O), monomers (M) and PNGase F-treated monomers (M*) are indicated. The position of molecular weight standard proteins are indicated at the left.

Figure 5:
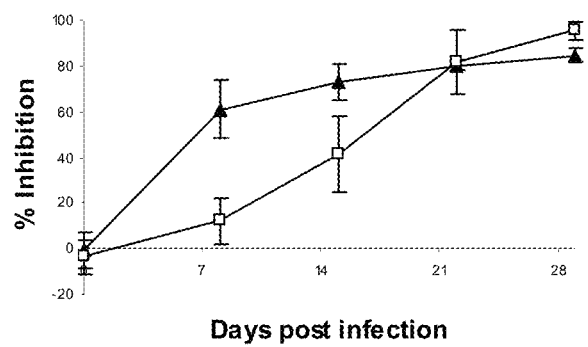
Figure 5:
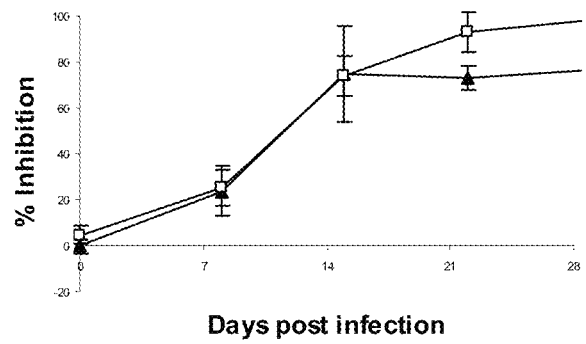
Figure 5:
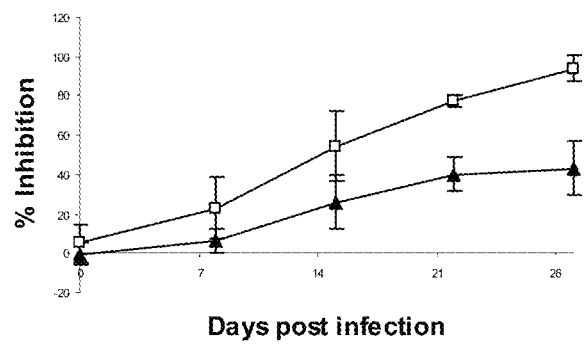

FIG. 5. Analysis of the E2 and $E^{RNS}$ antibody response by the Ceditest 2.0 E2 ELISA (▲) and the CHEKIT $E^{RNS}$ ELISA (□), respectively, induced by vFlc-34 (A), vFlc-N1 (B), or vFlc-ΔP(C). Values depicted are averages (n=4) with standard deviation.

Figure 6A:
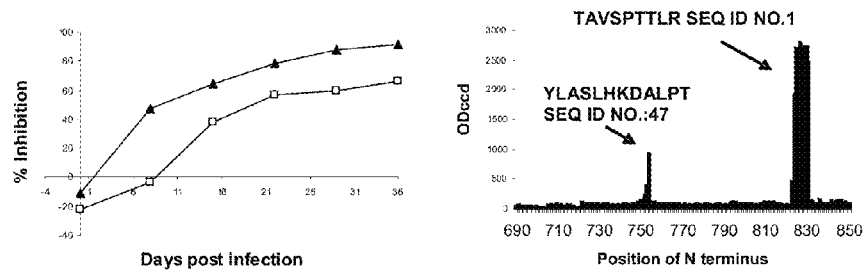
Figure 6B:
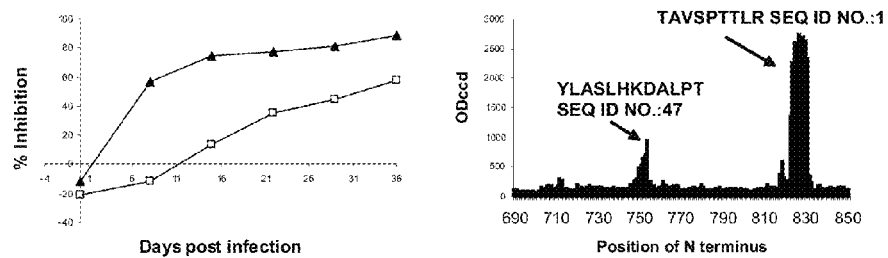
Figure 6C:
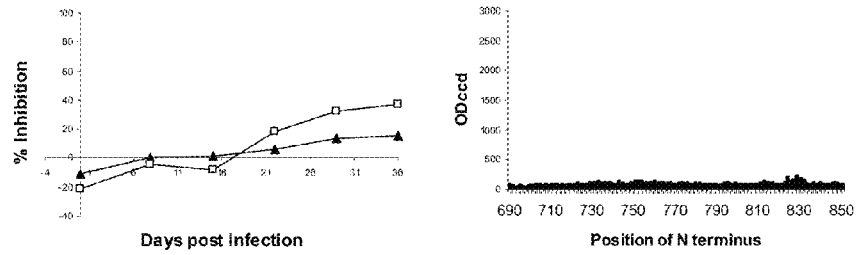
Figure 6D:
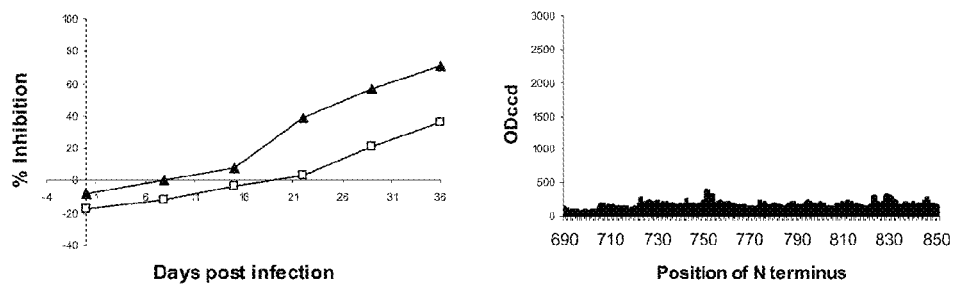
Figure 6E:
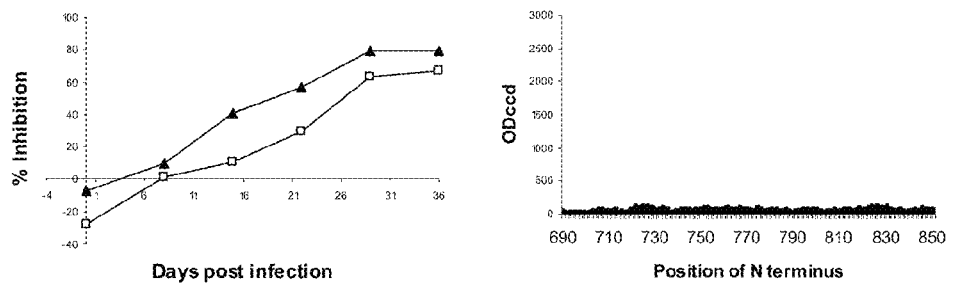
Figure 6F:
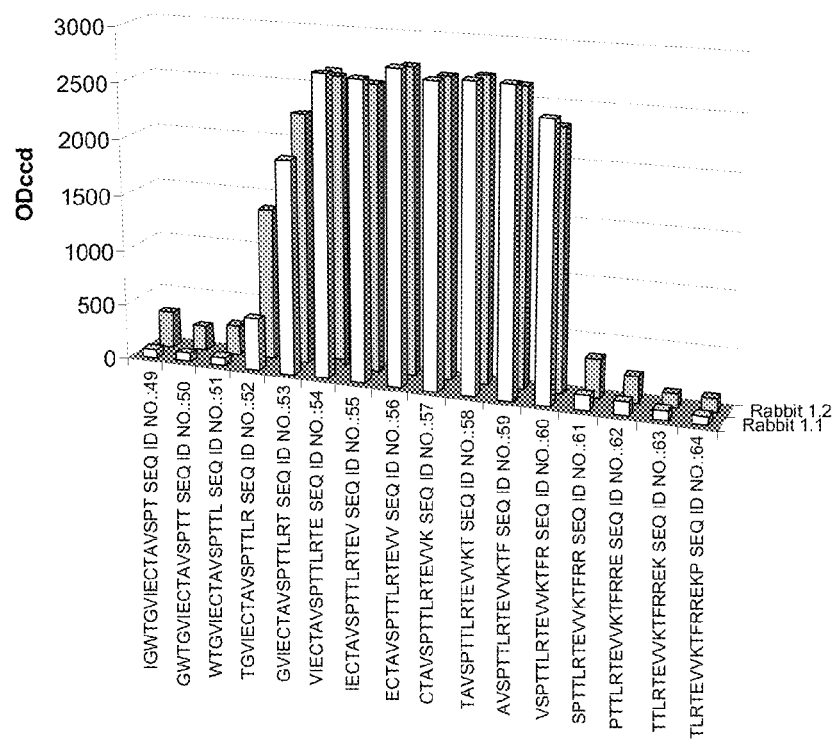
Figure 6G:
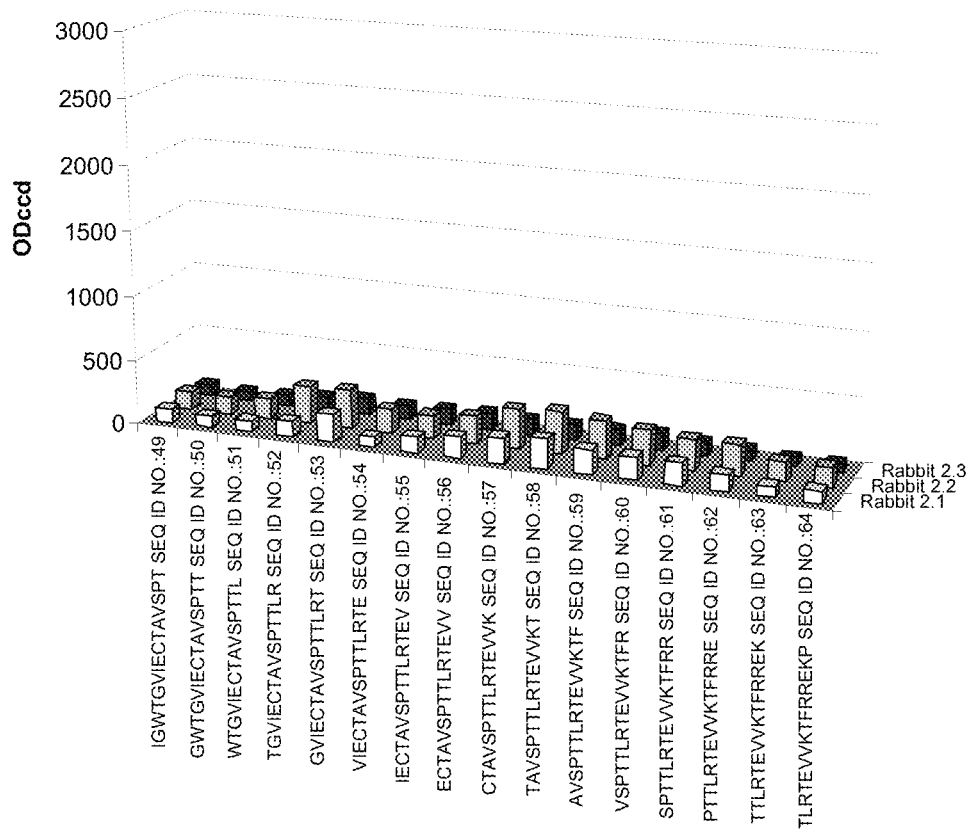

FIG. 6A-E. Left panels: Analysis of the E2 and $E^{RNS}$ antibody response by the Ceditest 2.0 E2 ELISA (▲) and the CHEKIT $E^{RNS}$ ELISA (□), respectively, induced by vFlc34 (Rabbits 1.1 (A) and 1.2 (B)) or vFlc-ΔPTa1 (Rabbits 2.1 (C), 2.2 (D) and 2.3 (E)). Right panels: Analysis of the rabbit antisera obtained at day 36 by PEPSCAN analysis. The reactivity of the rabbit antisera with 162 peptides (x-axis) is shown. The numbers on the x-axis correspond to the position of the peptide N termini in the CSFV polypeptide. The y-axis depicts the ODccd values. TAVSPTTLR (SEQ ID NO.:1); YLASLHKDALPT (SEQ ID NO.: 47);

FIG. 6F-G. Comparison of the reactivity of antibodies from rabbit antisera raised against vFlc34 (F) or vFlc-□PTa1 (G) with the TAVSPTTLR (SEQ ID NO.:1) epitope. The numbers on the x-axis correspond to the position of the peptide N termini in the CSFV polypeptide (SEQ ID NOs.: 49-64). The y-axis depicts the ODccd values.

Figure 7:
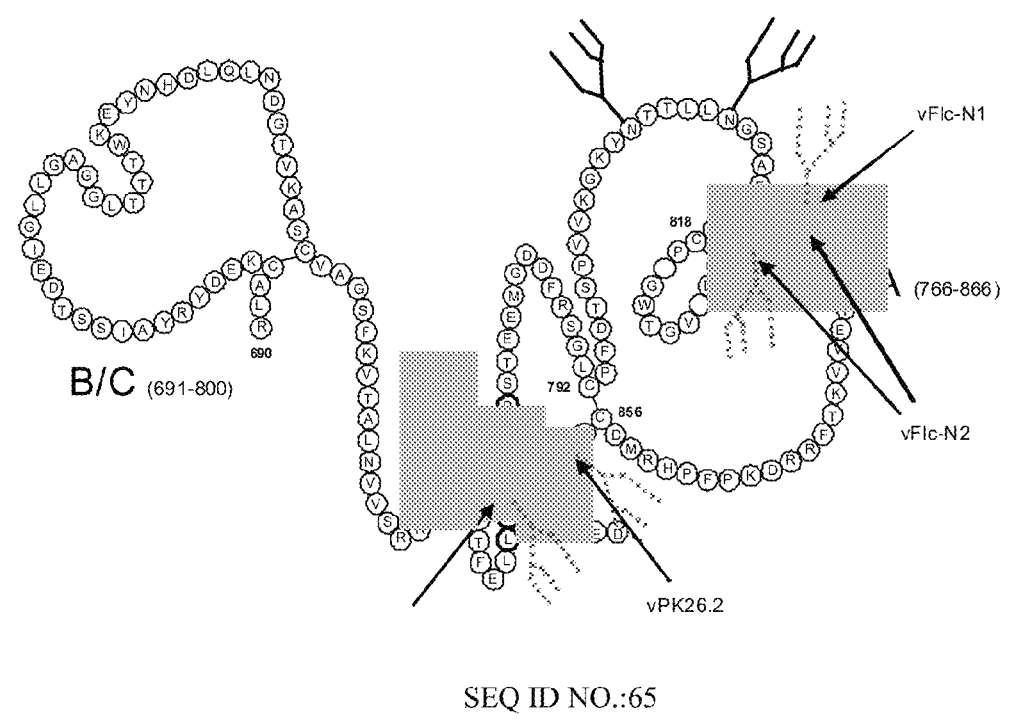

FIG. 7. Proposed antigenic structure of the ectodomain of the CSFV C-strain E2 protein (modified from Van Rijn et al., 1994. J Virol 68: 3934-42; SEQ ID NO: 65). Antigenic domains B/C and A are indicated. Positions of PNGSs referred to in the text are indicated by arrows. In these mutants the indicated amino acid is substituted for an Asn residue. Authentic N-linked glycans are drawn with solid lines, newly introduced (putative)N-linked glycans are drawn in dotted lines. Positions in E2 that are predicted to be co-localized in the native E2 structure are shaded. B-cell epitopes$^{829}$TAVSPTTLR$^{837}$ (SEQ ID NO.:1) and $^{772}$LFDGTNP$^{778}$ (SEQ ID NO.:5) are indicated in bold.

Figure 8:
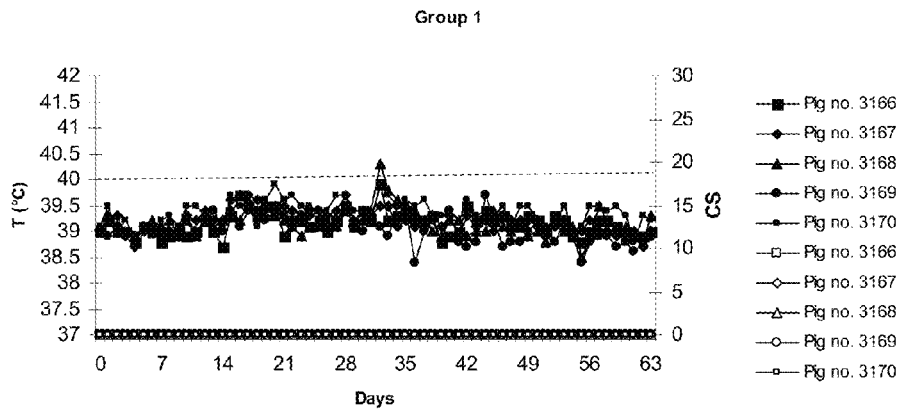
Figure 8:
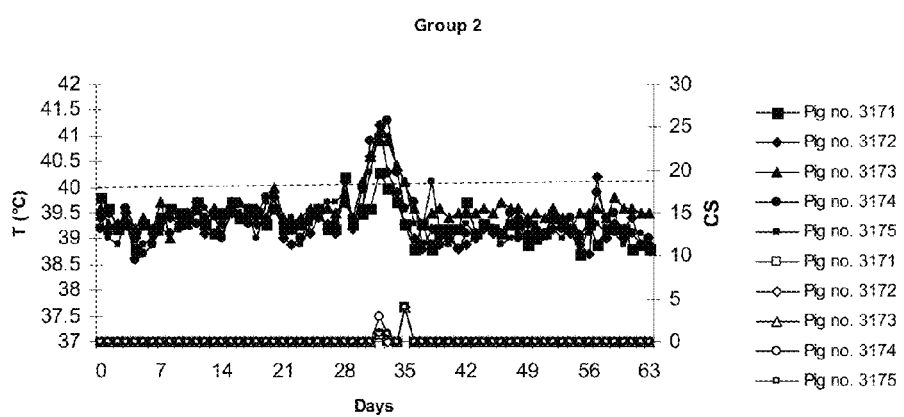
Figure 8:
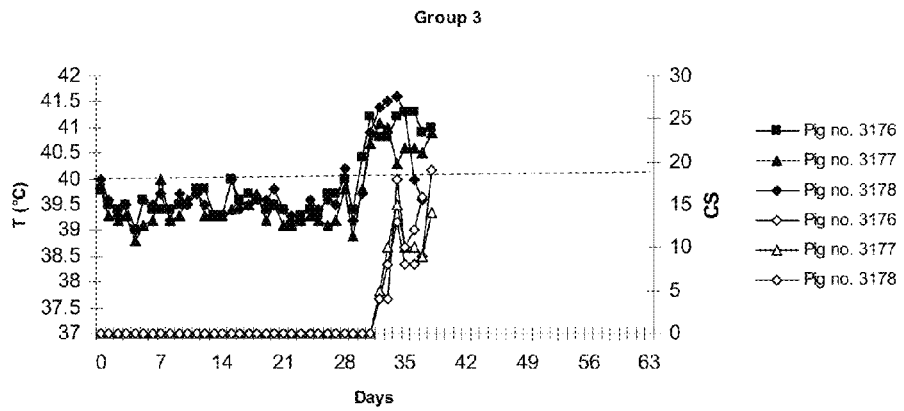

FIG. 8. Body temperatures (closed symbols) and clinical scores (CS; open symbols) of pigs vaccinated with vFlc34 (A; pig nos. 3166-3170), vFlc-ΔPTa1 (B; pig nos. 3171-3175) or pigs that were inoculated with culture medium only (C; pig nos. 3176-3178). Pigs were challenged with the virulent Brescia strain on day 28. Fever was defined as a body temperature above 40° C. (dotted line).

Figure 9:
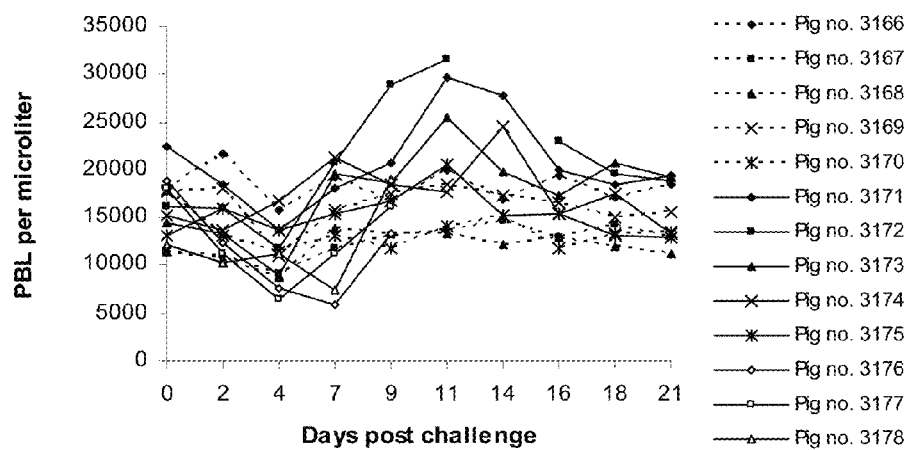
Figure 9:
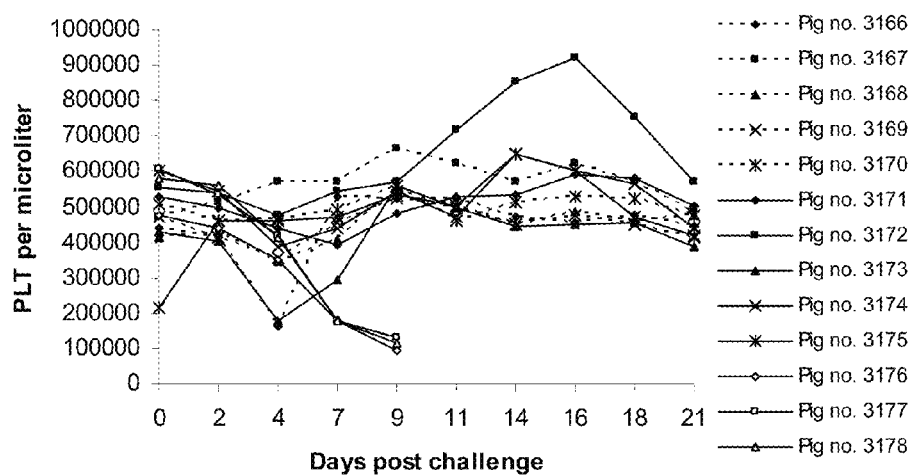

FIG. 9. Peripheral blood leukocyte (A) and platelet (B) counts in peripheral blood obtained from pigs challenged with a lethal dose of the highly virulent Brescia stain. At 28 days prior challenge, pigs were either inoculated with culture medium only, or vaccinated once with vFlc34 (pig nos. 3166-3170) or vFlc-ΔPTa1 (pig nos. 3171-3175).

Figure 10:
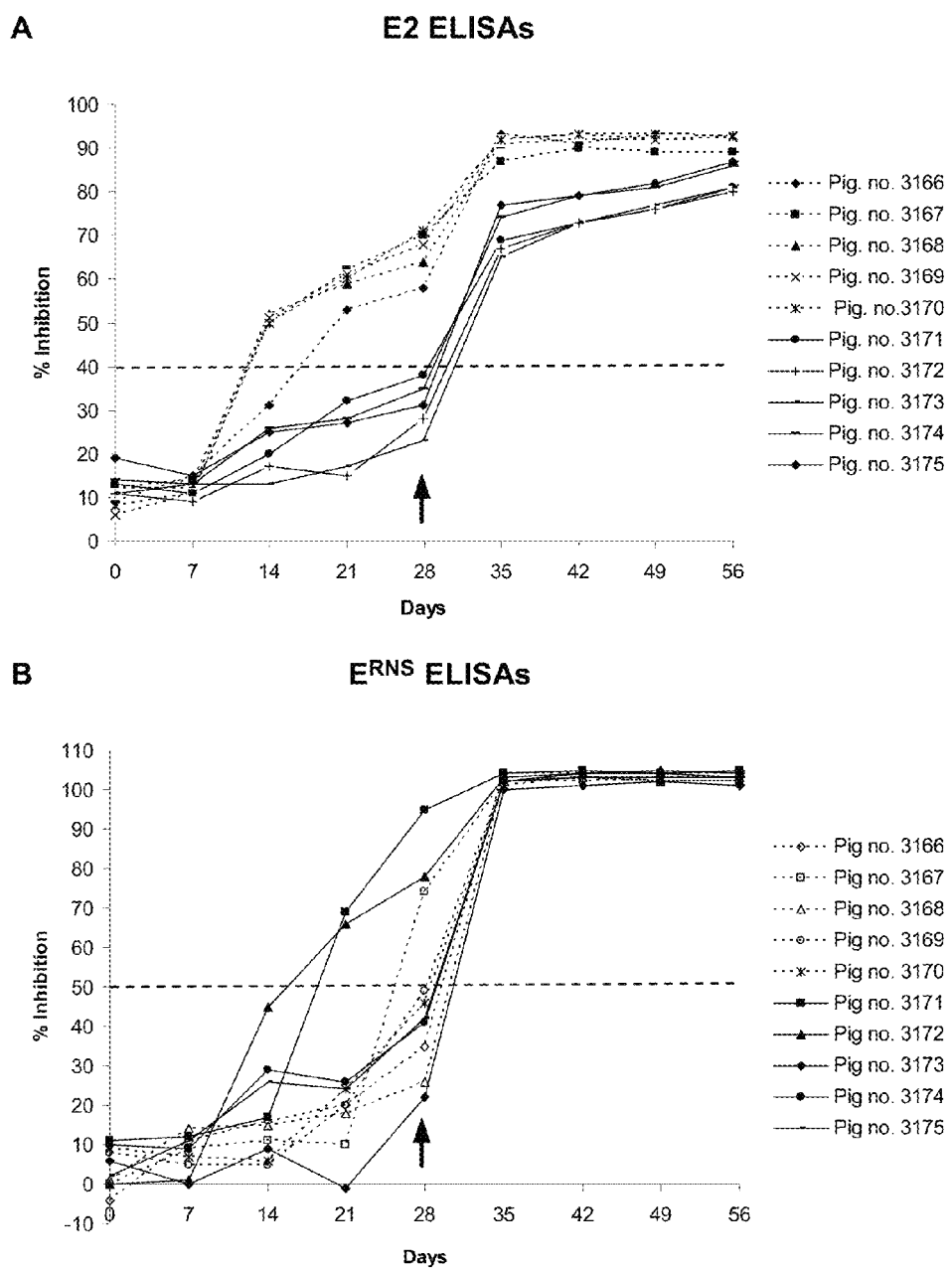

FIG. 10. Analysis of the antibody responses induced in pigs vaccinated with vFlc34 or vFlc-ΔPTa1 and subsequently challenged with the virulent Brescia strain. The PrioCHECK CSFV Ab 2.0 E2 ELISA (A) and the Chekit ERNS ELISA (B) were used for analysis of antibody responses. Sera that provide more than 40% or 50% blocking are considered positive for CSFV antibodies in the E2 ELISA and the ERNS ELISA, respectively. Pigs were vaccinated on day 0 with vFlc34 (pig nos. 3166-3170; interrupted lines) or vFlc-ΔPTa1 (pig nos. 3171-3175; solid lines) and were challenged on day 28 (arrow).

EXAMPLES

Example 1

Materials and Methods

Viruses and cells. Swine kidney cells constitutively expressing T7 RNA polymerase (SK6.T7) (van Gennip et al., 1999. J Virol Methods 78:117-28) were grown in K1000 medium supplemented with glutamine (0.3 mg/ml, Gibco), 5% fetal bovine serum and the antibiotics penicillin (100 U/ml, Gibco), streptomycin (100 U/ml, Gibco), amphotericin B (2.5 µg/ml, Gibco) and, when appropriate, with 10 mM L-histidinol dihydrochloride (Sigma). Unless indicated otherwise, virus stocks were produced by passaging the virus three to four times on SK6.T7 cells, followed by two successive freeze/thaw cycles of the infected monolayers. The latter was performed to maximize release of the C-strain virus, which is strongly cell-associated. Virus stocks were titrated on SK6.T7 cells in log 10 dilutions and were determined as TCID50/ml.

Construction of C-strain mutants. Plasmid pPRK-flc34, which contains a DNA copy of the "Cedipest" CSFV C-strain under T7-promoter control, was used as a template to introduce mutations by site-directed mutagenesis. The previously published DNA copy of the C-strain virus, named pPRKflc-133 (Moormann et al., 1996. J Virol 70:763-70) was found to lack a cytosine at the −10 position at the 3'-end of the genome. In pPRK-flc34, this error is corrected. Primers are described in Table 1. The name of the forward primer corresponds to the name of the constructed recombinant virus. Primer RV-r was used as a reverse primer for each construction. PCR amplification was performed using the Expand High-Fidelity PCR system (Roche). The PCR products were cloned into pGEM-T Easy vectors according to the instructions of the manufacturer (Promega) and sequenced using an ABI PRISM 310 genetic analyzer (Applied Biosystems). The PCR products were released from pGEM-T plasmids by digestion with ApaLI and used to replace the corresponding genome fragment of plasmid pPRc129, a pOK12-derived plasmid containing cDNA encoding the 5' half of the C-strain virus. The pPRc129 plasmids were subsequently digested with NotI and SalI, and the resulting fragments were used to replace the corresponding segment of plasmid pPRK-flc34, resulting in plasmids pFlc-N1, pFlc-N2, pFlc-N3, pFlc-N4, pFlc-N5, pFlc-ΔP, pFlc-ΔPT, pFlc-ASP, pFlc-ΔSPT, pFlc-ΔVSP, pFlc-ΔAVSP and pFlc-ΔSPTTL.

Virus production of C-strain mutants. Plasmids containing full-length cDNA clones were linearized with XbaI and transfected into SK6.T7 cells as described previously (van Gennip et al., 1999. J Virol Methods 78:117-28). Four days after transfection, expression of viral proteins was determined by immunoperoxidase monolayer assays (IPMA) using mAb WB103, which is directed against the CSFV non-structural protein NS3 (Edwards et al., 1991. Vet Microbiol 29:101-8). Cells from another well were treated with trypsin, transferred to a 25-cm2 tissue culture flask and grown for three to four days. When necessary, cells were passaged repeatedly to support virus growth. Monolayers were freeze-thawed, centrifuged to remove cell debris and subsequently stored at −70° C. The cleared lysates were used to prepare seedlots of the vaccine candidates by infecting fresh SK6.T7 cells followed by harvest four days later. Growth of the viruses was always performed on SK6.T7 cells. Although the viruses described here also replicated normally on SK6 cells, production yields were more accurately reproducible when using SK6.T7 cells.

To study the growth kinetics of the rescued viruses, subconfluent monolayers in 25-cm$^2$ tissue culture flasks were infected at a multiplicity of infection of 0.1. After 24, 48, 72, 96, 120, 144 and 168 hours post infection, the virus titers in cell lysates were determined. The material was freeze-thawed twice, clarified by centrifugation at 2,500×g at 4° C. and stored at −70° C. Virus titers (log TCID50/ml) were determined on SK6.T7 cells.

The E2 genes of the rescued viruses were sequenced. When appropriate, also the genes encoding the capsid (C), E$^{RNS}$ and E1 proteins (i.e. the structural proteins) were sequenced. To this end, viral RNA was isolated using the High Pure Total RNA isolation kit (Roche), and was used for cDNA synthesis using the Superscript First-Strand Synthesis system (Invitrogen) and a gene-specific primer. The cDNA was sequenced as described above.

Western blots. Lysates of infected SK6.T7 cells were prepared from confluent monolayers grown in 25-cm$^2$ tissue culture flasks. To this end, cells were lysed in 0.5 ml phosphate-buffered saline (PBS) containing 1% Nonidet P40 (BDH) and protease inhibitor cocktail (Complete, Roche). Celdebris was removed by centrifugation of 4 min at 10,000×g at 4° C. Proteins were separated in 12% polyacrylamide gels (NuPAGE system, Invitrogen) and subsequently transferred to nitrocellulose paper (Protran, Schleicher and Schuell). After blocking with PBS containing 0.05% Tween- and 1% Protifar (Nutricia), the blots were incubated with C-strain specific mAb C2, which is directed against the B/C domain of E2 (Bognár and Mészáros, 1963. Acta Vet Acad Sci Hung 13:429-438) and subsequently with peroxidase-conjugated rabbit anti-mouse immunoglobulins (DAKO). Peroxidase activity was detected with the enhanced chemiluminescense system (ECL Plus, GE Healthcare) using a Storm 860 molecular imager (GE Healthcare).

Immunoperoxidase monolayer assay (IPMA). Monolayers were washed with D-PBS (Gibco), dried to the air, and frozen at −20° C. The monolayers were fixed with paraformaldehyde (4% w/v in PBS) for 15 min and subsequently washed with PBS. Peroxidase-conjugated A domain-specific mAbs b2, b3, b4, b7 (Wensvoort et al., 1989. J Gen Virol 70: 2865-76), c1, c4, c8, c11 (Bognár and Mészáros, 1963. Acta Vet Acad Sci Hung 13:429-438) and the mAb used in the Ceditest 2.0 ELISA, named mAb 18.4, were used in PBS containing 0.05% Tween-80 (PBS-T) and 5% horse serum. After incubation at 37° C. for 1 h, the plates were washed three times with PBS-T after which activity of peroxidase was detected using 3-amino-9-ethyl-carbazole (AEC, Sigma) as the substrate.

Inoculation of rabbits. New Zealand white rabbits of approximately 2 kg were housed in groups of two to four animals. Body temperatures were monitored daily, starting from three days before the inoculation until five days after. The normal body temperature of rabbits varies from 38.5 to 40.1° C. Accordingly, fever was defined as a body temperature above 40.1° C. Rabbits were inoculated via the marginal ear vein with 200 µl growth medium containing 10$^3$ TCID50 of virus. Every seven days, serum was collected. EDTA blood, to be used for virus isolation, was collected four days after the inoculation.

Virus isolation. Peripheral blood leukocytes (PBLs) were concentrated from the EDTA blood samples by ammonium-chloride precipitation (0.83% NH$_4$Cl) as described (Terpstra and Wensvoort, 1988. Vet Microbiol 16:123-8). The PBLs were resuspended in PBS and frozen at −70° C. The next day, subconfluent SK6.T7 cell monolayers were incubated with the suspension of freeze-thawed PBLs for 1 h, after which the suspension was replaced by fresh growth medium, followed by an incubation period of four days. To produce sufficient virus for sequence analysis, the rescued viruses were passaged a few times on SK6.T7 cells.

PEPSCAN analysis. A complete set of overlapping 15 amino acid-long peptides derived from the CSFV strain Brescia E2 protein, spanning amino acids 690 to 851 of the CSFV polyprotein, were synthesized in credit-card format miniPEPSCAN cards as described previously (Geysen et al., 1984. Proc Natl Acad Sci USA 81:3998-4002). The binding of antibodies from sera to each peptide was tested in an ELISA based on pins as described by Slootstra et al. (Slootstra et al., 1996. Mol Divers 1:87-96).

Results

Production and characterization of C-strain mutants with newly introduced potential N-linked glycosylation sites (PNGSs). Full-length cDNA constructs encoding mutant C-strain viruses with newly introduced N-linked glycosylation sites in the TAVSPTTLR (SEQ ID NO.:1) epitope (FIG. 1) were constructed by genetic modification of pPRK-flc34, a cDNA clone of the "Cedipest" C-strain under T7 promoter control. The minimum requirement for N-linked glycosylation is the presence of the amino acid sequence asparagine (Asn)-X-threonine (Thr) or serine (Ser), where X can be any amino acid except Pro or aspartate (Asp) (Kornfeld and Kornfeld, 1985. Annu Rev Biochem 54:631-64). Mutant virus vFlc-N1 contains a single newly introduced PNGS, whereas mutants vFlc-N2, vFlc-N3, vFlc-N4 and vFlc-N5 contain multiple (FIG. 1). In vFlc-N5 virus, the central Pro residue of the TAVSPTTLR (SEQ ID NO.:1) epitope ($Pro^{833}$) is substituted for two Asn (N) residues, resulting in two overlapping PNGSs (i.e. NNTT (SEQ ID NO.:7)).

To produce recombinant virus, linearized plasmids were transfected into SK6.T7 cells, constitutively expressing T7 RNA polymerase. Four days after transfection, in all cases, the presence of infectious virus in the culture medium was demonstrated by infection of fresh SK6-T7 cells. However, large differences in viral fitness were noted. Although foci of infection of vFlc-N1 were somewhat smaller than those of vFlc34 (FIG. 2), multistep growth curves showed no significant difference in fitness of these two viruses (FIG. 3A). Virus vFlc-N2 was clearly more attenuated yielding considerably smaller foci and lower final titers (FIGS. 2 and 3A, respectively). Virus from the supernatant of cells transfected with pFlc-N3 or pFlc-N4 could be passaged once or twice, but were eventually lost. To provide the viruses with the opportunity to increase their fitness by mutation, cells containing these viruses were passaged repeatedly. Unfortunately, however, the number of positively stained cells did not increase during these passages, suggesting that no fitness compensating mutations were introduced.

Interestingly, the virus produced from pFlc-N5 (FIG. 1) could be rescued after only a few passages of transfected cells, eventually yielding a titre of $10^4$ TCID50/ml. The E2 gene of this virus was sequenced and was found to be unchanged. To produce vFlc-N5 in larger amounts, the virus was used to infect fresh SK6.T7 cells. Although this indeed resulted in titers similar to those normally obtained of vFlc34 (data not shown), consensus sequencing demonstrated that the virus had lost one of the two newly introduced Asn residues and was, thus, essentially identical to vFlc-N1. This finding suggests that a second Asn residue in the TAVSPTTLR (SEQ ID NO.:1) epitope is detrimental for the virus at some stage of the infection process. Consequently, only viruses vFlc-N1 and vFlc-N2 were considered suitable for further studies.

To be suitable as a DIVA vaccine, the vaccine candidate must be incapable of inducing A domain-specific antibodies in vivo. However, to get a first idea if the modifications introduced in the current candidates affected the antigenic structure of the A domain, we determined if the recombinant viruses could be recognized in IPMAs by any of our A domain-specific mAbs. The A domain-specific mAbs used were either raised against CSFV strain Brescia, (i.e. mAbs b2, b3, b4, b7) or the C-strain (i.e. c1, c4, c8 and c11). Also the mAb that is used in the Ceditest 2.0 ELISA, named mAb 18.4, was included in these experiments. Since some of our antibodies only weakly stained the wildtype C-strain, the ability of the antibodies to recognize the mutant C-strain viruses was studied by staining foci of infection, produced by growing the virus under methyl cellulose overlay. Whereas foci of infection of the wildtype C-strain were clearly stained by all antibodies used, these experiments demonstrated that the $Pro^{833} \rightarrow Asn$ substitution was sufficient to prevent recognition of the A domain by mAbs in vitro (data not shown).

Despite its exposure at the surface of the virion and the fact that it is a dominant target for neutralizing antibodies, the TAVSPTTLR (SEQ ID NO.:1) epitope of the A domain has been conserved throughout evolution. This suggests that viruses that contain this exact sequence have a selective advantage over variants within the virus population that contain amino acids substitutions in this region. Although we were successful in recovering viruses with either one (i.e. vFlc-N1) or two (i.e. vFlc-N2) newly introduced PNGSs in this epitope, it was of obvious relevance to study the evolution of these mutants upon growth in tissue culture. To this end, vFlc-N1 was passaged thirty times in vitro. To study the phenotypic stability of the virus, infected monolayers were immunostained with an antibody directed against the nonstructural protein NS3, named WB103, and duplicate monolayers were stained with a mixture of A domain-specific antibodies b3 and b4 to determine if phenotypic revertants (i.e. viruses of which the A domain could be stained with these antibodies) were present. After only three passages, a very small percentage of cells infected with vFlc-N1 were stained with the b3/b4 mixture, clearly indicating that phenotypic reversion occurred.

The general competitive exclusion principle of population biology states that when two organisms coexist in an environment in which resources are limited, one will eventually overgrow the other (Gause, 1934. Science 79:16-17). Considering this, we wanted to determine if the phenotypic revertant would overgrow vFlc-N1 by repeated passage of the virus. Strikingly, the amount of the phenotypic revertant remained at a very low level, in most experiments represented by only a few cells that were stained with the b3/b4 mAb mixture. It thus appeared that the phenotypic revertant virus was continuously created, but was always maintained as a minority variant in the virus population. Since this finding suggested a lower fitness of the phenotypic revertant relative to that of vFlc-N1, we considered it unlikely that the revertant virus represented a true reversion to the wildtype C-strain sequence. To identify the mutation that was responsible for the revertant phenotype, the virus population needed to be enriched for the revertant virus in order to be able to sequence its genome. By seeding dilutions of the virus in 96-well plates, populations that were enriched for the phenotypic revertants could be selected. After repeating this selection, a population was obtained which contained sufficient amounts of the revertant virus to determine its genome sequence. In two individual experiments, the phenotypic revertant was shown to contain a Ser residue at the position where the Asn was introduced (i.e. position 833 of the CSFV polyprotein), resulting from a single transition in the Asn codon (from AAU to AGU). Since this mutation results in a loss of the PNGS, it is not surprising that it was accompanied by a restored ability of mAbs to recognize the A domain. In conclusion, the detection of the revertant subpopulation demonstrates that vFlc-N1 explored possibilities to increase its fitness by mutation. However, since the newly introduced AAU codon was maintained by the master genotype, the virus is considered genetically stable on the population level.

Analysis of vFlc-N2 revealed phenotypic variants with similar characteristics as those observed during experiments with vFlc-N1, but these were not further characterized.

Analysis of the relative electrophoretic mobilities of E2 proteins with one or multiple newly introduced PNGSs. To determine if the newly introduced PNGSs in the TAVSPTTLR (SEQ ID NO.:1) epitope of vFlc-N1 and vFlc-N2 resulted in the attachment of new carbohydrate moieties to E2, the relative electrophoretic mobilities of the modified E2 proteins were studied by polyacrylamide gel electrophoresis (PAGE) under reducing conditions followed by Western blotting. Western blots containing separated proteins of cells infected with vFlc34, vFlc-N1 and vFlc-N2 demonstrated that the E2 protein of vFlc-N1 was of higher molecular weight than the corresponding protein of vFlc34 (FIG. 4). Also oligomers containing E2 were detected, however, considering that the proteins were analyzed under denaturing conditions, these oligomers are probably not physiological (FIG. 4). Treatment of the cell lysates with PNGase F, an enzyme that removes N-linked glycans from proteins, yielded E2 proteins of identical molecular weight.

Western blots containing separated proteins of vFlc-N2 suggested that at least one of the two newly introduced glycosylation sequons is used as an anchor site for a carbohydrate moiety (FIG. 4). These lysates seemed also to contain E2 proteins of even higher molecular weight, suggesting glycosylation of the second glycosylation site.

Production and characterization of C-strain mutants with targeted deletions in the TAVSPTTLR (SEQ ID NO.:1) epitope. Full-length cDNA constructs encoding C-strain viruses with targeted deletions in the TAVSPTTLR (SEQ ID NO.:1) epitope (FIG. 1) were constructed as described above for glycosylation mutants. Deletion of the central Pro residue of the TAVSPTTLR (SEQ ID NO.:1) epitope yielded vFlc-ΔP, which produced somewhat smaller foci of infection as compared to vFlc34 (FIG. 2) and grew in most experiments to 10-fold lower titers (FIG. 3B). The highest titers obtained however exceeded $10^6$ TCID50/ml. Analysis of vFlc-EP by IPMAs demonstrated that this C-strain mutant was not detected by any of our A domain-specific mAbs. Notably, after 20 passages, consensus sequencing demonstrated a transition mutation in the $Ser^{789}$ codon (from UCC to UUC), which resulted in the substitution of Ser for phenylalanine (Phe). The resulting virus was named vFlcΔPa1 (FIG. 1).

In contrast to vFlc-ΔP, viruses with deletions of more than one amino acid were highly debilitated. Similar as already described for glycosylation mutants vFlc-N3 and vFlc-N4, virus from the supernatant of cells transfected with plasmids encoding these viruses could be passaged a few times, but were subsequently lost. To provide the viruses with the opportunity to increase their fitness by mutation, cells transfected with these constructs were passaged repeatedly. Passage of cells transfected with pFlc-ΔSP, pFlc-ΔSPT, pFlc-ΔVSP, pFlc-ΔAVSP and pFlc-ΔSPTTL did not result in an increase in virus production.

During initial passages of cells transfected with pFlc-ΔPT, the results were similar to those obtained with the other deletion constructs, yielding foci of infection that were of constant small size (average of 10-20 cells). However, after a few additional passages, immune staining demonstrated a sudden improved growth of the virus, which suggested that the virus had introduced fitness compensating mutations. The resulting virus was named vFlc-ΔPTa1. To identify putative resuscitating mutations in vFlc-ΔPTa1, the consensus sequence of its E2 gene was determined. Remarkably, this demonstrated that the virus had retained the introduced deletion and had introduced two mutations in the E2 gene. Conveniently, a clear double peak in the sequence chromatogram of one of the mutations suggested that a transition mutation resulting in a codon change from GAC to AAC was the first to occur (data not shown). This mutation resulted in the substitution of $Asp^{774}$ to Asn and, interestingly, introduced a new PNGS in the A domain of E2 (FIGS. 1 and 7). The second change was a transversion within the valine (Val)-831 codon of the TAVSPTTLR (SEQ ID NO.:1) epitope (from GUG to GGG), which resulted in a Val to glycine (Gly) substitution.

Considering the possibility that adaptive mutations could also be present in genes encoding other structural proteins, also the consensus sequence of the C, $E^{RNS}$ and E1 genes were determined. Sequence analysis of the C gene and the $E^{RNS}$ gene revealed only a single silent mutation in the latter (U1549→C). Interestingly, in the E1 gene, a transversion mutation at position 2275 (A2275→U) was detected that resulted in the substitution of glutamic acid (Glu)-634 for an aspartic acid (Asp) (Table 2).

The in vitro growth characteristics of vFlc-ΔPTa1, relative to vFlc34 and vFlc-ΔP, is visualized by multistep growth curves (FIG. 3). Although the vFlc-ΔPTa1 virus grows somewhat slower than vFlc34, identical final titers are obtained.

Experimental evolution of viruses produced form plasmid pFlc-ΔPT. The results obtained from sequence analysis of vFlc-ΔPTa1 led us to suggest that the silent mutation in $E^{RNS}$, the amino acid substitution in E1 and the two substitutions in E2 were responsible for fitness recovery. To test this hypothesis, ten independent transfections with pFlc-ΔPT were performed and the genes encoding the structural proteins were sequenced. The transfected cells were passaged repeatedly and the presence of virus was monitored by IPMAs using mAb WB103. After only two to three passages, the number of positive cells clearly increased, suggesting that the viruses had introduced fitness compensating mutations. After eleven passages, the genomes of the viruses were analyzed as described for vFlc-ΔPTa1. The results of this experiment are summarized in Table 2. The mutation that resulted in the $Asp^{774}$→Asn substitution was found in six out of ten evolved viruses, clearly demonstrating parallel evolution. However, in one of these viruses, a mutation was found that results in a $Asp^{774}$→Glu substitution and in the three remaining viruses, no mutation was found in the codon of amino acid 774. The mutation that was responsible for the $Val^{831}$→Gly in vFlc-ΔPTa1 was detected in one virus (i.e. vFlc-ΔPTa8, Table 2).

Interestingly, the silent mutation at position 1549 was found in all viruses. This result suggests that natural selection also operated at the RNA level and that additional adaptive mutations can possibly be found in regions of the genome that were not analyzed in this experiment. However, it was striking to find that three of four mutations detected in the genome of vFlc-ΔPTa1 were again introduced during evolution of the viruses in the current experiment. Of note, in virus vFlc-ΔPTa5 a mutation at a fifth position was detected. Besides the silent mutation in the $E^{RNS}$ gene and the $Asp^{774}$→Asn substitution in E2, this virus had introduced a transition mutation in the $Ala^{445}$ codon (from GCA to ACA) of the $E^{RNS}$ gene, which resulted in the substitution of $Ala^{445}$ for Thr (Table 2).

Analysis of the antibody response against vFlc-ΔP and vFlc-N1. The inability of A domain-specific antibodies to recognize vFlc-ΔP and vFlc-N1 in vitro demonstrated that we were successful in modifying the antigenic structure of the A domain. However, to be suitable as a DIVA vaccine, the antibody response induced in vivo must be sufficiently dampened to be able to serologically differentiate infected from vaccinated animals. Although the vaccine candidates will ultimately be tested for their DIVA property and protective efficacy in pigs, in the current work, we preferred using rabbits for analysis of the humoral immune response, for two main reasons. First, we wanted to determine if the vaccine viruses under study are capable of a productive infection in vivo. In pigs, inoculation of C-strain viruses does not induce any clinical symptoms, whereas inoculation in rabbits induces a temporal febrile illness. Hence, using rabbits enabled us to confirm productive infection and furthermore allowed us to study potential differences in virulence of the selected candidates, which could provide some idea of fitness of the viruses in vivo (de Smit, et al., 2000. Vaccine 18:2351-8). A second advantage of using rabbits is that the C-strain virus can be isolated from the blood, which is often unsuccessful when using pigs. The isolation of the vaccine virus after replication in vivo allowed us to determine if the introduced genetic modifications were stably maintained. Groups of four rabbits were inoculated with vFlc-ΔP or vFlc-N1. Control animals were inoculated with either vFlc34 or culture medium. During the days of the acclimatization period, the average body temperatures of the rabbits were normal (39.2° C., SD±0.28, n=68). Fever was defined as a body temperature above 40.1° C. Fever was first noted in the groups inoculated with vFlc34 (40.7° C., SD±0.48, n=4) and vFlc-N1 (40.5° C., SD±0.32, n=4), both at two days after inoculation. An elevated body temperature in rabbits inoculated with vFlc-ΔP (40.0° C., SD±0.13, n=4) was noted at three days after inoculation.

Virus was isolated from PBLs of three of four rabbits inoculated with vFlc34, three of four rabbits inoculated with vFlc-N1 and two of four rabbits inoculated with vFlc-ΔP. Consensus sequencing demonstrated that the E2 genes of these viruses were not altered by the passage in rabbits. To determine if the C-strain mutants enable the differentiation between infected and vaccinated animals, the rabbit antisera were analyzed by the Ceditest 2.0 E2 ELISA (Prionics). This ELISA specifically detects antibodies against the A domain of E2. As a reference control for effective immunization, the CHEKIT CSF $E^{RNS}$ ELISA (IDEXX laboratories) was used.

The $E^{RNS}$ responses induced by vFlc34, vFlc-N1 and vFlc-ΔP were comparable (FIG. 5). Comparing the A domain-specific E2 responses induced by vFlc34 and vFlc-N1 by the Ceditest 2.0 ELISA demonstrated that the modification present in vFlc-N1 had a minor effect on this response. In contrast, comparing the E2 responses of vFlc-ΔP with that of vFlc34 demonstrated that the deletion of Pro$^{833}$ did result in a quantitative shift in the antibody response against the A domain (FIG. 5). Considering the disappointing effect of the newly introduced N-linked glycosylation site of vFlc-N1 on the A domain-specific antibody response, we did not study the antigenic properties of vFlc-N2 in rabbits, but instead focused on the deletion mutants for further experiments.

Analysis of the antibody response against vFlc-ΔPTa1. In the second animal trail, the antibody response against vFlc-ΔPTa1 was compared with that induced against vFlc34. The average body temperature of the rabbits prior inoculation was normal (39.2° C., SD±0.37, n=28). In this experiment, only one of two rabbits inoculated with vFlc34 experienced fever at two days after inoculation (40.3° C.). One rabbit (rabbit 2.1) that was inoculated with vFlc-ΔPTa1 did not show any elevation in body temperature. In contrast, fever was noted in the remaining two animals inoculated with vFlc-ΔPTa1 (rabbits 2.2 and 2.3). In one of these animals a temperature was noted of 40.6° C. at five days post inoculation, whereas in the other rabbit a temperature was noted of 40.4° C. at seven days post inoculation. Considering the fact that vFlc-ΔP did not induce fever, this finding was highly unexpected. It is important to note, however, that shortly after inoculation, rabbits 2.2 and 2.3 were involved in a quarrel that resulted in the affliction of wounds. Considering that these wounds induced an infection of the skin and the fact that the symptoms of this infection coincided with the occurrence of fever, it is plausible to assume that the fever resulted from the skin infection, rather than being a consequence of the virus inoculation. At four days after inoculation, virus was isolated from both animals inoculated with vFlc34. No virus was isolated from PBLs of the three rabbits inoculated with vFlc-ΔPTa1, which is likely related to the attenuation of this virus.

The sera of the two rabbits that were inoculated with vFlc34 (animals 1.1 and 1.2; FIG. 6, left panel) gave results in the $E^{RNS}$ and E2 ELISA that were comparable to those obtained in the first experiment. The blocking percentages determined by the E2 ELISA were higher than those detected by the $E^{RNS}$ ELISA. In contrast, analysis of sera from rabbit 2.1, which was inoculated with vFlc-ΔPTa1, demonstrated that the blocking percentages in the E2 ELISA were lower than those detected in the $E^{RNS}$ ELISA. This result is in line with the results obtained with vFlc-ΔP (FIG. 5), both demonstrating a specific dampening of the A domain-specific antibody response. Unexpectedly, however, analysis of sera from animals 2.2 and 2.3 did not confirm this result. These animals clearly developed high levels of A domain-specific E2 antibodies. Considering the results obtained with animal 2.1 and earlier results obtained with vFlc-ΔP, this finding was very surprising. The induction of A domain-specific antibodies in animals 2.2 and 2.3 can possibly be explained by a refocusing of the A domain-specific antibody response towards epitopes of the A domain other than the TAVSPTTLR (SEQ ID NO.:1) epitope, which are normally subdominant.

To analyze the antibody responses more thoroughly, we made use of PEPSCAN analysis using previously constructed 15 amino acid-long overlapping peptides derived from the E2 protein of CSFV strain Brescia. This analysis revealed that the sera obtained at day 36 from animals inoculated with the wildtype C-strain recognized two epitopes of CSFV strain Brescia (FIG. 6, right panel). As expected, the first of these epitopes was the $^{829}$TAVSPTTLR$^{837}$ (SEQ ID NO.:1) epitope. Particularly, residues $^{831}$VSPTTLR$^{837}$ (SEQ ID NO.:9) appeared most critical (FIG. 6B, top panel). The second epitope comprised amino acids $^{754}$YLASLHKDAPT$^{764}$ (SEQ ID NO.:10). Interestingly, this epitope, which is recognized for the first time, is located outside the previously defined A domain (i.e. amino acids 766-866; FIG. 7). None of the sera obtained from rabbits inoculated with vFlc-ΔPTa1 recognized either of the abovementioned epitopes. Although the lack of recognition of the $^{829}$TAVSPTTLR$^{837}$ (SEQ ID NO.:1) epitope (FIG. 6B, bottom panel) can be explained by the mutations introduced in vFlc-ΔPTa1, the lack of recognition of the $^{754}$YLASLHKDAPT$^{764}$ (SEQ ID NO.:10) epitope was more surprising. This finding suggests that the $^{754}$YLASLHKDAPT$^{764}$ epitope in some way interacts with the $^{829}$TAVSPTTLR$^{837}$ (SEQ ID NO.:1) epitope and that these epitopes are located in proximity in the native E2 structure (FIG. 7).

Although PEPSCAN analysis did not reveal the epitopes of the A domain that are recognized by the antisera of rabbits 2.2 and 2.3, it did demonstrated that neither of these sera recognized the TAVSPTTLR epitope. From this, we can conclude that vFlc-ΔPTa1 fulfils the DIVA criterion when accompanied by a TAVSPTTLR-based peptide ELISA.

Discussion

In the past two decades, several experimental DIVA vaccines were developed that need either be accompanied by an E2 or an $E^{RNS}$ ELISA. It is often stated in literature that both diagnostic tests are suitable for the detection of CSF in the field. Although this is in principal correct, it is important to note that $E^{RNS}$ ELISAs have two major disadvantages over E2 ELISAs. First, although $E^{RNS}$ ELISAs can be used to reliable detect infected herds, these ELISAs were previously found to be insufficiently sensitive to diagnose individual animals. Second, and much more importantly, $E^{RNS}$ ELISAs are not CSF-specific (2003/265/EC). SANCO/10809/2003. European Commission, Directorate-General for Health and Consumer Protection, Brussels). Consequently, use of E$^{RNS}$ ELISAs in regions where BVDV and/or BDV viruses circulate is not recommended.

The objective of the current work was to construct a C-strain-based DIVA vaccine that is compatible with an E2 ELISA. We aimed to achieve this by introducing judicious mutations in the TAVSPTTLR (SEQ ID NO.:1) epitope of the A domain, which is the dominant target in these ELISAs. In the first of two approaches, the central Pro (i.e. Pro$^{833}$) residue of the TAVSPTTLR (SEQ ID NO.:1) epitope was substituted for Asn, thereby introducing a PNGS in the center of the TAVSPTTLR (SEQ ID NO.:1) epitope. Although N-linked glycans are well known for their ability to shield immunogenic domains from the humoral immune system, they can be remarkably well tolerated at or near functionally important domains, two features that are attributed to the structural flexibility of the carbohydrate chain. Although we were successful in producing a C-strain mutant, named vFlc-N1, that stably maintains a newly introduced N-linked glycan anchored to the center of the TAVSPTTLR (SEQ ID NO.:1) epitope, this modification seemed to have an only minor effect on the A domain-specific antibody response. For this reason, we chose not to continue this approach.

In an alternative approach, we aimed to alter the antigenic structure of the A domain by deleting amino acids from the TAVSPTTLR (SEQ ID NO.:1) epitope. Deletion of the central Pro residue (i.e. Pro$^{833}$) yielded a virus, named vFlc-ΔP, that stably maintained the introduced deletion, although the virus eventually acquired an adaptive mutation, resulting in the substitution of Ser$^{789}$ to phenylalanine (Phe). We found this nonconservative substitution interesting, since Ser$^{789}$ is present in all C-strain viruses and related lapinized CSFV strains, whereas Phe$^{789}$ is completely conserved in virulent CSFV strains and even highly conserved among other members of the pestivirus genus (van Rijn et al., 1997. Virology 237:337-48). Although the history of the C-strain virus is not well documented, it is clear that the virus was attenuated by passage in rabbits hundreds of times (van Oirschot, 2003. Vet Microbiol 96:367-84). It could therefore be hypothesized that Ser$^{789}$ is advantageous for replication of the C-strain in rabbits. If this assumption is correct, it is interesting to reason why the C-strain does not revert to Phe$^{789}$ upon growth on porcine cells in vitro. This can be explained by the fitness landscape concept of Wright (Wright, 1931. Genetics 16:97-159). According to this concept, advantageous mutations arise slowly when a genotype exists at the top region of a fitness peak, as likely applies for the wildtype C-strain virus, whereas these arise more quickly when the genotype exists at a lower level of a fitness peak, as is the case for vFlc-ΔP.

Analysis of sera obtained from rabbits inoculated with vFlc-ΔP demonstrated that the deletion of Pro$^{833}$ is already sufficient to considerably dampen the immunogenicity of the A domain. Although this result demonstrated proof of principle of our approach, it also made clear that the antigenic structure of the A domain needed to be more extensively modified to render the resulting virus suitable as a DIVA vaccine. Although plasmids encoding C-strain mutants with deletions of two to four amino acids from the TAVSPTTLR (SEQ ID NO.:1) epitope (ΔSP, ΔPT, ΔSPT, ΔVSP, ΔAVSP) produced infectious virus, these were highly debilitated and incapable of sustained growth. After a few passages of cells containing vFlc-ΔPT, however, a remarkable increase in fitness was noted. The rescued virus was named vFlc-ΔPTa1. We considered it most likely that adaptive mutations in the E2 gene were responsible for fitness-recovery. Indeed, two adaptive mutations were detected in the E2 gene (FIG. 1). The first mutation resulted in the substitution of the Val residue of the TAVSPTTLR (SEQ ID NO.:1) epitope for Gly. Although adaptive mutations that are in close proximity of the introduced deletion might have been expected, a second mutation was found to be located distal to the TAVSPTTLR (SEQ ID NO.:1) epitope in the linear E2 sequence. It was furthermore interesting to note that this second mutation (Asp$^{774}$→Asn) introduced a PNGS in the A domain.

The rescue of a C-strain mutant with a PNGS in the A domain (i.e. vFlc-ΔPTa1, FIGS. 1 and 7) shortly after constructing a similar virus by reverse genetics (i.e. vFlc-N1; FIGS. 1 and 7), seems a remarkable coincidence. Looking back at previous findings that prompted us to initiate our studies, however, suggests that our findings may not be coincidental. Our work was inspired by the phenotype of a CSFV mutant that was selected for by growing the virus in the presence of neutralizing mAbs (van Rijn, et al., 1994. J Virol 68:3934-42). This MAR (monoclonal antibody-resistant) mutant of strain Brescia, named vPK26.2, had two amino acid substitutions in E2 that affected the antigenic structure of the A domain, namely Pro$^{833}$→Leu (within the TAVSPTTLR (SEQ ID NO.:1) epitope) and a Thr$^{858}$→Asn (24). Analysis of also other MAR mutants demonstrated that the Pro$^{833}$→Leu substitution was responsible for neutralization escape and furthermore interfered with binding of a second A domain-specific mAb. However, although a MAR mutant that contained only Leu$^{833}$ was still recognized by two other A domain-specific mAbs, MAR mutant vPK26.2, which contained both Leu$^{833}$ and Asn$^{858}$, was not detected by any of our A domain-specific mAbs. Considering that Asn$^{858}$ clearly affected the antigenic structure of the A domain, we hypothesized that position$^{858}$ in some way interacts with, or is in close proximity to, the TAVSPTTLR (SEQ ID NO.:1) epitope in the native E2 structure. It is furthermore interesting to note that the Thr$^{858}$→Asn substitution introduced a new PNGS in the A domain (FIG. 7). Although glycosylation at this site was not previously addressed, the effect of this mutation on the antigenic structure of E2 could be explained by a shielding of the A domain by an N-linked glycan. The phenotype of vPK26.2 prompted us to investigate not only the effect of deleting the central Pro of the TAVSPTTLR (SEQ ID NO.:1) epitope, but also to study the feasibility of shielding the A domain by N-linked glycans. We found it convenient that substituting Pro$^{833}$ for Asn, which resulted in virus vFlc-N1, removes the structurally important Pro$^{833}$ residue, and simultaneously introduces a new PNGS in the TAVSPTTLR (SEQ ID NO.:1) epitope. It is important to note that this modification can be regarded as a replacement of Pro$^{833}$ by Asn, but can also be regarded as an insertion of an Asn residue in a virus that lacks Pro$^{833}$. Although this seems a matter of semantics, it opens up an entirely new perspective that could explain the phenotype of vPK26.2 as well as the genetic stability and fitness of vFlc-N1. A striking common feature of these viruses is that they both lack Pro$^{833}$ and both contain a new PNGS in the A domain. From this, it is tempting to speculate that positions 833 and 858 are in fact located at similar positions in the native E2 structure, and that a Asn moiety at either one of these positions, directly or by virtue of its function as an anchor site for a carbohydrate moiety, can compensate for the fitness cost imposed by the deletion or substitution of Pro$^{833}$ (FIG. 7).

Coming back to virus vFlc-ΔPTa1, it is interesting to note that the newly introduced PNGS in vFlc-ΔPTa1 at position 774 might also be located in proximity of the TAVSPTTLR (SEQ ID NO.:1) epitope in the native E2 structure. Namely, the Asp$^{774}$→Asn substitution in this virus is located at the center of a recently identified epitope comprising amino acids $^{772}$LFDGTNP$^{778}$ (SEQ ID NO.:5) (Peng et al., 2008. Virus Res 135: 267-72). Like the $^{829}$TAVSPTTLR$^{837}$ (SEQ ID NO.: 1) epitope, the $^{772}$LFDGTNP$^{778}$ (SEQ ID NO.:5) epitope shares all three features that define the A1 domain, being CSFV-specific, evolutionarily conserved and a target for neutralizing antibodies. Based on the aforementioned and our experimental findings, we hypothesize that the TAVSPTTLR and the LFDGTNP epitope are co-localized in the native structure of E2 and, possibly, together make up the A1 domain.

In summary, we hypothesize that a mutation of the central Pro residue of the TAVSPTTLR (SEQ ID NO.:1) epitope can be compensated by N-linked glycans located at one of three possible positions in the E2 protein, and that these positions are located in proximity in the native E2 structure. The first is located within the $^{829}$TAVSPTTLR$^{837}$ (SEQ ID NO.:1) epitope itself, the second in the $^{772}$LFDGTNP$^{778}$ (SEQ ID NO.:5) epitope and the third domain includes the amino acid sequence $^{858}$TTT$^{860}$ (FIG. 7). Possibly, the latter amino acids are also part of an as yet unidentified epitope located in the A domain. Experiments are in progress to substantiate these hypotheses.

Although it is plausible to assume that the adaptive mutations in the E2 gene play an important role in fitness recovery, we reasoned that also mutations in other genes encoding structural proteins could play a role. Therefore, also the C, E$^{RNS}$ and E1 genes of vFlc-ΔPTa1 were sequenced. Sequencing of this part of the genome indeed revealed two additional mutations. The first was detected in the E1 gene. This mutation resulted in the substitution of the completely conserved Glu$^{634}$ residue for Asp. Considering that the E2 protein is known to assemble into disulphide-linked heterodimers with the E1 protein (Thiel, et al., 1991. J Virol 65:4705-12), it is conceivable that this mutation contributed to the fitness recovery of vFlc-ΔPTa1. Although no mutations were detected in the C gene, a single silent mutation was detected in the E$^{RNS}$ gene. Bearing in mind that the consensus sequence of wildtype CSFV is exceptionally stable, accumulating virtually no mutations upon passage in vitro or in vivo (Vanderhallen, et al., 1999. Arch Virol 144:1669-77), the detection of such a silent mutation by consensus sequencing demonstrated that natural selection also operated at the RNA level, and thereby that also synonymous mutations in other regions of the genome could have contributed to the fitness recovery of vFlc-ΔPTa1.

To gain insight into the molecular pathway of fitness recovery, an evolution experiment was performed. This experiment demonstrated parallel evolution of the silent mutation in the E$^{RNS}$ gene, the mutation that resulted in the Val$^{831}$→Gly substitution and the mutation that introduced the new PNGS at position 774 (Table 2). Although additional studies are clearly required to fully elucidate the molecular mechanism of fitness recovery, this finding supports the notion that the aforementioned mutations were indeed involved in the fitness recovery of vFlc-ΔPTa1. It is very well possible that these mutations can restore the fitness of mutants with larger deletions in the TAVSPTTLR (SEQ ID NO.:1) epitope.

Worth mentioning, in one of the viruses studied in the evolution experiment (i.e. vFlc-ΔPTa5), a mutation was detected in the E$^{RNS}$ gene that resulted in the substitution of Ala$^{445}$ to Thr (Table 2). Like the previously described Ser$^{789}$ to Phe substitution found upon the evolution of vFlc-ΔP, the amino acid that is altered in vFlc-ΔPTa5, in this case Ala$^{445}$, is changed into an amino acid that is conserved among CSFV field strains, in this case Thr$^{445}$. Although this finds beyond the scope of the current work, this finding again demonstrates that attenuation of CSFV can provide valuable insights into its molecular evolution.

Previous studies with MAR mutants performed by Van Rijn et al., suggested that Pro$^{833}$ and Thr$^{834}$ of the TAVSPTTLR (SEQ ID NO.:1) epitope are very important for the integrity of conserved epitopes of the A domain (van Rijn, et al., 1994. J Virol 68:3934-42). The successful production of a well growing C-strain mutant that lacks both these amino acids and, in addition, contains a Val$^{831}$→Gly substitution, suggested that the antigenic structure of the A domain of this virus was changed dramatically. We therefore expected that the immune response induced by vFlc-ΔPTa1 would be distinguishable from that induced by wildtype CSFV using the Ceditest 2.0 E2 ELISA. It was surprising to find that vFlc-ΔPTa1 can actually be quite potent in inducing A domain-specific antibodies. A possible explanation for this finding is that the disruption of the otherwise immunodominant TAVSPTTLR (SEQ ID NO.:1) epitope can result in a refocusing of the antibody response towards epitopes of the A domain that are normally subdominant. In an attempt to identify these epitopes, the antisera were analyzed by PEPSCAN analysis. Although this analysis did not reveal the newly recognized epitopes, it did demonstrate that none of the antisera recognized peptides containing the TAVSPTTLR (SEQ ID NO.:1) epitope. Interestingly, this suggests that an ELISA based on the TAVSPTTLR (SEQ ID NO.:1) epitope can be used as a DIVA test to accompany the vFlc-ΔPTa1 vaccine virus.

In summary, the current work demonstrates that forced virus evolution can be a powerful tool to genetically modify the CSF virus. Here, this method was successfully employed to produce a genetically stable C-strain mutant that can be serologically differentiated from wildtype CSFV.

Example 2

Materials and Methods

The C-strain deletion mutant virus vFlc-ΔPTa1 was produced as described in Example 1. SK6-T7 cells are swine kidney cells that constitutively express T7 RNA polymerase (van Gennip et al., 1999. Vaccine 19(4-5), 447-59). These cells were grown in K1000 medium supplemented with glutamine (0.3 mg/ml, Gibco, Invitrogen, Breda, The Netherlands), 5% fetal bovine serum (FBS) and the antibiotics penicillin (100 U/ml, Gibco), streptomycin (100 U/ml, Gibco) and amphotericin B (2.5 µg/ml, Gibco). Virus stocks were titrated on SK6.T7 cells and are reported as 50% tissue culture infective doses(TCID$_{50}$).

Thirteen conventional pigs free of antibodies against pestiviruses were divided into two groups of five pigs and one group of three pigs. Pigs from group 1 (nos. 3166-3170) were vaccinated once on day 0 via the intramuscular route with 1 ml of culture medium containing 2% fetal bovine serum (FBS) and 10$^5$ TCID50 of the recombinant C-strain virus vFlc34 (see Example 1). Pigs from group 2 (nos. 3171-3175) were vaccinated, by the same protocol, with the vFlc-ΔPTa1 vaccine. Pigs from group 3 (nos. 3176-3178) were inoculated once with culture medium containing 2% FBS.

On day 28, pigs from groups 1, 2 and 3 were challenged intranasally with 1 ml (0.5 ml each nostril) containing 200× the 50% lethal doses of CSFV strain Brescia. All pigs were observed daily for disease and their body temperatures were measured starting at day −3. The severity of clinical symptoms was scored using a previously defined list of 10 CSF-specific criteria (Mittelholzer et al., 2000. Vet Microbiol 74(4), 293-308).

Serum samples were prepared weekly from all pigs. EDTA samples and oropharyngeal fluids were collected from all pigs of groups 1, 2 and 3 at the day of challenge (day 28) and subsequently on days 30, 32, 35, 37, 39, 42, 44, 46, 49, 52 and 56. EDTA samples were used to determine the number of leukocytes and thrombocytes. This analysis was performed with the Medonic CA 620 coulter counter (Boule Medical AB). In conventional reared pigs, leukocyte and thrombocyte concentrations in the blood range between $11 \times 10^9$ and $23 \times 10^9$ and between $320 \times 10^9$ and $720 \times 10^9$/liter, respectively. Consequently, leukopenia was defined as $<8 \times 10^9$ celles/l blood and thrombocytopenia as $<200 \times 10^9$ thrombocytes/l blood.

Virus isolation and quantitative real-time reverse-transcription PCR (qRRT-PCR) using peripheral blood leukocytes (PBLs) or throat swabs were performed essentially as described (Weesendorp et al., 2009. Vet Microbiol 135(3-4), 222-30).

Serum samples were analyzed using a commercial E2 ELISA (PrioCHECK CSFV Ab 2.0 E2 ELISA, Prionics, Lelystad, The Netherlands) and a commercial $E^{RNS}$ ELISA (Chekit CSF $E^{RNS}$ ELISA, IDEXX laboratories, Hoofddorp, The Netherlands), according to the instructions of the manufacturers.

Results

We compared the protective efficacy of the vFlc-ΔPTa1 virus with its parental virus, vFlc34, against a lethal challenge with the highly virulent Brescia strain. Two groups of five pigs were vaccinated on day 0 with either vFlc34 (group 1) or with vFlc-ΔPTa1 (group 2). A control group (group 3), consisting of three pigs, was inoculated with cell culture medium only. Pigs from groups 1, 2 and 3 were challenged with the highly virulent Brescia strain on day 28.

All pigs in the control group developed typical clinical signs of CSF, including high fever (FIG. 8C), leukopenia (FIG. 9A) and thrombocytopenia (FIG. 9B). Virus was isolated from PBLs of two of three pigs on day 4 and of all three pigs on days 7 and 9 post challenge. Virus was isolated from throat swabs of two animals on day 7 post challenge and from one animal on day 9 post challenge. Pigs from this group were found in a moribund state and were euthanized 9 days (pig 3178) or 10 days (pigs 3176 and 3177) post infection.

None of the pigs vaccinated with the recombinant C-strain vaccine (i.e. vFlc34) developed clinical signs after challenge (FIG. 8A), although one pig (no. 3168) had fever for one day and one other pig (no. 3166) displayed thrombocytopenia for at least one day (FIG. 9B). No virus was isolated from PBLs or throat swabs.

All pigs that were vaccinated with vFlc-ΔPTa1 developed fever for 3 to 6 days and displayed mild clinical signs after challenge (FIG. 8B), but all pigs fully recovered. Virus was isolated from PBLs of one pig (pig no. 3175) on day 2 post challenge. From this, we conclude that a single vaccination with vFlc-ΔPTa1 provides protection against a lethal challenge with the highly virulent Brescia strain.

All sera were analyzed for the presence of anti-E2 and anti-$E^{RNS}$ antibodies with the PrioCHECK CSFV Ab 2.0 E2 ELISA (Prionics) and the Chekit CSF $E^{RNS}$ ELISA (IDEXX laboratories), respectively. All pigs vaccinated with vFlc34 were positive in the E2 ELISA at 21 days p.i. (FIG. 10A) whereas these pigs were positive in the $E^{RNS}$ ELISA at 35 days p.i. (FIG. 10B). None of the pigs vaccinated with vFlc-ΔPTa1 were positive in the E2 ELISA before challenge (FIG. 10A). Within 7 days after challenge, all pigs were positive in the E2 ELISA (FIG. 10A). It is interesting to note that two pigs (i.e. pigs 3171 and 3172) vaccinated with vFlc-ΔPTa1 seroconverted for $E^{RNS}$ antibodies much earlier than those vaccinated with vFlc34 (FIG. 10B).

Thus, it is concluded that all pigs vaccinated with vFlc-ΔPTa1 remained below the cut-off of the PrioCHECK E2 ELISA until challenge, showing that vFlc-ΔPTa1 can be used as a DIVA vaccine also in pigs.

In conclusion, we demonstrate that a single vaccination with vFlc-ΔPTa1 provided protection against a highly virulent challenge in all vaccinated pigs and evidence is provided that very little or no virus shedding occurred.

TABLES

TABLE 1

Primers used to construct C-strain mutants

| Primer | Sequence[a] | |
|---|---|---|
| RV-N1 | 5'-GA<u>GTGCAC</u>AGCAGTGAGCAATACAACTCTGAGAACAGAAG-3' | (SEQ ID NO.: 12) |
| RV-N2 | 5'-GA<u>GTGCAC</u>AAATGTGAGCAATACAACTCTGAGAACAGAAGTGGTAAAGACCTTC-3' | (SEQ ID NO.: 13) |
| RV-N3 | 5'-GA<u>GTGCAC</u>AGCAGTGAGCAATACAACTAATAGAACAGAAGTGGTAAAGACCTTCAGGAGA-3' | (SEQ ID NO.: 14) |
| RV-N4 | 5'-GA<u>GTGCAC</u>AAATGTGAGCAATACAACTAATAGAACAGAAGTGGTAAAGACCTTC-3' | (SEQ ID NO.: 15) |
| RV-N5 | 5'-GA<u>GTGCAC</u>AGCAGTGAGCAATAATACAACTCTGAGAACAGAAG-3' | (SEQ ID NO.: 16) |
| RV-ΔP | 5'-GA<u>GTGCAC</u>AGCAGTGAGCACAACTCTGAGAACAGAAGTGGTAAAGACC-3' | (SEQ ID NO.: 17) |
| RV-ΔPT | 5'-GA<u>GTGCAC</u>AGCAGTGAGCACTCTGAGAACAGAAGTGGTAAAGACC-3' | (SEQ ID NO.: 18) |
| RV-ΔSP | 5'-GA<u>GTGCAC</u>AGCAGTGACAACTCTGAGAACAGAAGTGGTAAAGACCTTC-3' | (SEQ ID NO.: 19) |
| RV-ΔSPT | 5'-GA<u>GTGCAC</u>AGCAGTGACTCTGAGAACAGAAGTGGTAAAGACCTTC-3' | (SEQ ID NO.: 20) |
| RV-ΔVSP | 5'-GA<u>GTGCAC</u>AGCAACAACTCTGAGAACAGAAGTGGTAAAGACC-3' | (SEQ ID NO.: 21) |
| RV-ΔAVSP | 5'-GA<u>GTGCAC</u>AACAACTCTGAGAACAGAAGTGGTAAAGACC-3' | (SEQ ID NO.: 22) |
| RV-ΔSPTTL | 5'-GA<u>GTGCAC</u>AGCAGTGAGAACAGAAGTGGTAAAGACCTTCCAGGAGA-3' | (SEQ ID NO.: 23) |
| RV-r | 5'-CTCTGTCTTCACAGACGG<u>TGCAC</u>-3' | (SEQ ID NO.: 24) |

[a]ApaLI restriction sites (underlined) and nucleotide substitutions (bold) are indicated.

TABLE 2

Sequence determination[a] of the C, E1, E$^{RNS}$ and E2 genes of independently evolved viruses produced from pFlc-ΔPT[b].

| Virus: | Mutation: | Codon change: | Amino acid change: | ORF: |
|---|---|---|---|---|
| ΔPTa1 | U1549 → C | GUU → GUC | none | E$^{RNS}$ |
|  | A2275 → U | GAA → GAU | E634 → D | E1 |
|  | G2693 → A | GAC → AAC | D774 → N | E2 |
|  | U2865 → G | GUG → GGG | V831 → G | E2 |
| ΔPTa2 | U1549 → C | GUU → GUC | none | E$^{RNS}$ |
|  | C2695 → A | GAC → GAA | D774 → E | E2 |
| ΔPTa3 | U1549 → C | GUU → GUC | none | E$^{RNS}$ |
|  | G2693 → U | GAC → AAC | D774 → N | E2 |
| ΔPTa4 | U1549 → C | GUU → GUC | none | E$^{RNS}$ |
| ΔPTa5 | U1549 → C | GUU → GUC | none | E$^{RNS}$ |
|  | G1706 → A | GCA → ACA | A445 → T | E$^{RNS}$ |
|  | G2693 → U | GAC → AAC | D774 → N | E2 |
| ΔPTa6 | U1549 → C | GUU → GUC | none | E$^{RNS}$ |
|  | G2693 → U | GAC → AAC | D774 → N | E2 |
| ΔPTa7 | U1549 → C | GUU → GUC | none | E$^{RNS}$ |
|  | G2693 → U | GAC → AAC | D774 → N | E2 |
| ΔPTa8 | U1549 → C | GUU → GUC | none | E$^{RNS}$ |
|  | U2865 → A | GUG → GGG | V831 → G | E2 |
| ΔPTa9 | U1549 → C | GUU → GUC | none | E$^{RNS}$ |
| ΔPTa10 | U1549 → C | GUU → GUC | none | E$^{RNS}$ |
|  | G2693 → U | GAC → AAC | D774 → N | E2 |
| ΔPTa11 | U1549 → C | GUU → GUC | none | E$^{RNS}$ |
|  | G2693 → U | GAC → AAC | D774 → N | E2 |

[a]Identified mutations are indicated in bold.
[b]The in vitro growth characteristics of virus vFlc-ΔPTa1 are depicted in FIGS. 2 and 3b. The growth characteristics of the other viruses were not determined.

---

The invention claimed is:

1. An infectious replication competent recombinant classical swine fever virus (CSFV), comprising a deletion in a "TAVSPTTLR" (SEQ ID NO: 1) domain of the E2 protein of classical swine fever virus, corresponding to amino acid positions 829 to 837 of a parental CSFV polyprotein; wherein said deletion is selected from the group consisting of P833, T834, and P833 and T834.

2. The recombinant CSFV of claim 1, wherein said deletion comprises a deletion of the proline (P833) in said "TAVSPT-TLR" (SEQ ID NO.:1) domain.

3. The recombinant CSFV according to claim 1, comprising at least one further alteration of the parental genome.

4. The recombinant CSFV according to claim 3, wherein the at least one further alteration is a silent mutation.

5. A recombinant classical swine fever virus (CSFV), comprising a deletion of at least one amino acid in a "TAVSPT-TLR" (SEQ ID NO: 1) domain of the E2 protein corresponding to position 829 to 837 of a parental CSFV polyprotein; and further comprising a silent mutation that is a U to C alteration at position 1549 in the $E^{RNS}$ gene.

6. A recombinant classical swine fever virus (CSFV), comprising a deletion of at least one amino acid in a "TAVSPTTLR" (SEQ ID NO: 1) domain of the E2 protein, corresponding to position 829 to 837 of a parental CSFV polyprotein that comprises at least one further alteration of the parental genome; wherein the at least one further alteration results in a glycine (G) at position 831, and/or a phenylalanine (F) at position 789, and/or a threonine (T) at position 445; and/or forms a N-linked glycosylation site in the E2 protein.

7. The recombinant CSFV according to claim 3, wherein said at least one further alteration is a substitution of aspartic acid (D) at position 774 in the E2 protein.

8. The recombinant CSFV according to claim 1, comprising at least one further alteration; wherein said at least one further alteration results in a glycine (G) at position 831, and/or a phenylalanine (F) at position 789, and/or a threonine (T) at position 445.

9. The recombinant CSFV according to claim 1, comprising a deletion of proline and threonine at position 833 and 834, respectively, of the "TAVSPTTLR" (SEQ ID NO: 1) domain of the E2 protein, and further comprising a U to G alteration at position 1549, an aspartic acid (D) at position 634, an asparagine (N) at position 774 in the E2 protein, and a glycine (G) at position 831.

10. The recombinant CSFV according to claim 1 wherein the CSFV comprises a genome of an attenuated CSFV strain.

11. The recombinant CSFV according to claim 1 wherein the CSFV comprises a genome of a C (Chinese)-strain.

12. A live CSF vaccine comprising a recombinant CSFV according to claim 1.

13. A method of protecting an animal against CSF, comprising administering to said animal an effective amount of the vaccine of claim 12.

14. A cDNA molecule comprising an infectious replication competent recombinant classical swine fever virus (CSFV) genome encoding an E2 protein of classical swine fever virus, and comprising a deletion of at least one amino acid in a "TAVSPTTLR" (SEQ ID NO: 1) domain; wherein said deletion is selected from the group consisting of P833, T834, and P833 and T834.

15. The recombinant CSFV according to claim 1, comprising at least one further alteration; wherein the at least one further alteration is a silent mutation; and wherein the silent mutation is a U to C alteration at position 1549 in the $E^{RNS}$ gene.

16. The recombinant CSFV according to claim 1, comprising at least one further alteration; wherein the at least one further alteration forms a N-linked glycosylation site in the E2 protein.

* * * * *

SEQUENCE LISTING

<160> NUMBER OF SEQ ID NOS: 65

<210> SEQ ID NO 1
<211> LENGTH: 9
<212> TYPE: PRT
<213> ORGANISM: Artificial
<220> FEATURE:
<223> OTHER INFORMATION: classical swine fever virus E2 domain

<400> SEQUENCE: 1

Thr Ala Val Ser Pro Thr Thr Leu Arg
1               5

<210> SEQ ID NO 2
<211> LENGTH: 4
<212> TYPE: PRT
<213> ORGANISM: Artificial
<220> FEATURE:
<223> OTHER INFORMATION: CSFV E2 domain

<400> SEQUENCE: 2

Ala Val Ser Pro
1

<210> SEQ ID NO 3
<211> LENGTH: 5
<212> TYPE: PRT
<213> ORGANISM: Artificial
<220> FEATURE:
<223> OTHER INFORMATION: CSFV E2 domain

<400> SEQUENCE: 3

Ser Pro Thr Thr Leu
1               5

```
<210> SEQ ID NO 4
<211> LENGTH: 12
<212> TYPE: DNA
<213> ORGANISM: Artificial
<220> FEATURE:
<223> OTHER INFORMATION: attenuating oligonucleotide

<400> SEQUENCE: 4
cuuuuuucuu uu                                                              12

<210> SEQ ID NO 5
<211> LENGTH: 7
<212> TYPE: PRT
<213> ORGANISM: Artificial
<220> FEATURE:
<223> OTHER INFORMATION: CSFV E2 domain

<400> SEQUENCE: 5

Leu Phe Asp Gly Thr Asn Pro
1               5

<210> SEQ ID NO 6
<211> LENGTH: 4
<212> TYPE: PRT
<213> ORGANISM: Artificial
<220> FEATURE:
<223> OTHER INFORMATION: heterologous control peptide

<400> SEQUENCE: 6

Asx Val Asp Val
1

<210> SEQ ID NO 7
<211> LENGTH: 4
<212> TYPE: PRT
<213> ORGANISM: Artificial
<220> FEATURE:
<223> OTHER INFORMATION: domain in vFlc-N5 virus

<400> SEQUENCE: 7

Asn Asn Thr Thr
1

<210> SEQ ID NO 8
<211> LENGTH: 4
<212> TYPE: PRT
<213> ORGANISM: Artificial
<220> FEATURE:
<223> OTHER INFORMATION: introduced PNGS in TAVSPTTLR

<400> SEQUENCE: 8

Asn Asn Thr Thr
1

<210> SEQ ID NO 9
<211> LENGTH: 7
<212> TYPE: PRT
<213> ORGANISM: Artificial
<220> FEATURE:
<223> OTHER INFORMATION: CSFV epitope

<400> SEQUENCE: 9

Val Ser Pro Thr Thr Leu Arg
1               5

<210> SEQ ID NO 10
<211> LENGTH: 11
```

```
<212> TYPE: PRT
<213> ORGANISM: Artificial
<220> FEATURE:
<223> OTHER INFORMATION: CSFV epitope

<400> SEQUENCE: 10

Tyr Leu Ala Ser Leu His Lys Asp Ala Pro Thr
1               5                   10

<210> SEQ ID NO 11
<211> LENGTH: 7
<212> TYPE: PRT
<213> ORGANISM: Artificial
<220> FEATURE:
<223> OTHER INFORMATION: CSFV epitope

<400> SEQUENCE: 11

Leu Phe Asp Gly Thr Asn Pro
1               5

<210> SEQ ID NO 12
<211> LENGTH: 40
<212> TYPE: DNA
<213> ORGANISM: Artificial
<220> FEATURE:
<223> OTHER INFORMATION: primer

<400> SEQUENCE: 12
gagtgcacag cagtgagcaa tacaactctg agaacagaag                         40

<210> SEQ ID NO 13
<211> LENGTH: 54
<212> TYPE: DNA
<213> ORGANISM: Artificial
<220> FEATURE:
<223> OTHER INFORMATION: primer

<400> SEQUENCE: 13
gagtgcacaa atgtgagcaa tacaactctg agaacagaag tggtaaagac cttc         54

<210> SEQ ID NO 14
<211> LENGTH: 60
<212> TYPE: DNA
<213> ORGANISM: Artificial
<220> FEATURE:
<223> OTHER INFORMATION: primer

<400> SEQUENCE: 14
gagtgcacag cagtgagcaa tacaactaat agaacagaag tggtaaagac cttcaggaga   60

<210> SEQ ID NO 15
<211> LENGTH: 54
<212> TYPE: DNA
<213> ORGANISM: Artificial
<220> FEATURE:
<223> OTHER INFORMATION: primer

<400> SEQUENCE: 15
gagtgcacaa atgtgagcaa tacaactaat agaacagaag tggtaaagac cttc         54

<210> SEQ ID NO 16
<211> LENGTH: 43
<212> TYPE: DNA
<213> ORGANISM: Artificial
<220> FEATURE:
<223> OTHER INFORMATION: primer
```

<400> SEQUENCE: 16
gagtgcacag cagtgagcaa taatacaact ctgagaacag aag         43

<210> SEQ ID NO 17
<211> LENGTH: 48
<212> TYPE: DNA
<213> ORGANISM: Artificial
<220> FEATURE:
<223> OTHER INFORMATION: primer

<400> SEQUENCE: 17
gagtgcacag cagtgagcac aactctgaga acagaagtgg taaagacc    48

<210> SEQ ID NO 18
<211> LENGTH: 45
<212> TYPE: DNA
<213> ORGANISM: Artificial
<220> FEATURE:
<223> OTHER INFORMATION: primer

<400> SEQUENCE: 18
gagtgcacag cagtgagcac tctgagaaca gaagtggtaa agacc       45

<210> SEQ ID NO 19
<211> LENGTH: 48
<212> TYPE: DNA
<213> ORGANISM: Artificial
<220> FEATURE:
<223> OTHER INFORMATION: primer

<400> SEQUENCE: 19
gagtgcacag cagtgacaac tctgagaaca gaagtggtaa agaccttc    48

<210> SEQ ID NO 20
<211> LENGTH: 45
<212> TYPE: DNA
<213> ORGANISM: Artificial
<220> FEATURE:
<223> OTHER INFORMATION: primer

<400> SEQUENCE: 20
gagtgcacag cagtgactct gagaacagaa gtggtaaaga ccttc       45

<210> SEQ ID NO 21
<211> LENGTH: 42
<212> TYPE: DNA
<213> ORGANISM: Artificial
<220> FEATURE:
<223> OTHER INFORMATION: primer

<400> SEQUENCE: 21
gagtgcacag caacaactct gagaacagaa gtggtaaaga cc          42

<210> SEQ ID NO 22
<211> LENGTH: 39
<212> TYPE: DNA
<213> ORGANISM: Artificial
<220> FEATURE:
<223> OTHER INFORMATION: primer

<400> SEQUENCE: 22
gagtgcacaa caactctgag aacagaagtg gtaaagacc              39

<210> SEQ ID NO 23
<211> LENGTH: 46

```
<212> TYPE: DNA
<213> ORGANISM: Artificial
<220> FEATURE:
<223> OTHER INFORMATION: primer

<400> SEQUENCE: 23
gagtgcacag cagtgagaac agaagtggta aagaccttcc aggaga            46

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
ctctgtcttc acagacggtg cac                                     23

<210> SEQ ID NO 25
<211> LENGTH: 20
<212> TYPE: PRT
<213> ORGANISM: Artificial
<220> FEATURE:
<223> OTHER INFORMATION: CSFV E2 domain wild-type

<400> SEQUENCE: 25

Leu Phe Asp Gly Thr Asn Pro Ser Thr Glu Glu Met Gly Asp Asp Phe
1               5                   10                  15

Arg Ser Gly Leu
            20

<210> SEQ ID NO 26
<211> LENGTH: 20
<212> TYPE: PRT
<213> ORGANISM: Artificial
<220> FEATURE:
<223> OTHER INFORMATION: CSFV E2 domian mutant vFlc-deltaPa1

<400> SEQUENCE: 26

Leu Phe Asp Gly Thr Asn Pro Ser Thr Glu Glu Met Gly Asp Asp Phe
1               5                   10                  15

Arg Phe Gly Leu
            20

<210> SEQ ID NO 27
<211> LENGTH: 20
<212> TYPE: PRT
<213> ORGANISM: Artificial
<220> FEATURE:
<223> OTHER INFORMATION: CSFV E2 domain mutant vFlc-deltaPTa1

<400> SEQUENCE: 27

Leu Phe Asn Gly Thr Asn Pro Ser Thr Glu Glu Met Gly Asp Asp Phe
1               5                   10                  15

Arg Ser Gly Leu
            20

<210> SEQ ID NO 28
<211> LENGTH: 20
<212> TYPE: PRT
<213> ORGANISM: Artificial
<220> FEATURE:
<223> OTHER INFORMATION: CSFV E2 domain mutant vFlc-deltaPTa2

<400> SEQUENCE: 28
```

```
Leu Phe Glu Gly Thr Asn Pro Ser Thr Glu Glu Met Gly Asp Asp Phe
1               5                   10                  15

Arg Ser Gly Leu
            20
```

<210> SEQ ID NO 29
<211> LENGTH: 19
<212> TYPE: PRT
<213> ORGANISM: Artificial
<220> FEATURE:
<223> OTHER INFORMATION: CSFV E2 domain wild-type

<400> SEQUENCE: 29

```
Thr Gly Val Ile Glu Cys Thr Ala Val Ser Pro Thr Thr Leu Arg Thr
1               5                   10                  15

Glu Val Lys
```

<210> SEQ ID NO 30
<211> LENGTH: 19
<212> TYPE: PRT
<213> ORGANISM: Artificial
<220> FEATURE:
<223> OTHER INFORMATION: CSFV E2 domain mutant vFlc-N1

<400> SEQUENCE: 30

```
Thr Gly Val Ile Glu Cys Thr Ala Val Ser Asn Thr Thr Leu Arg Thr
1               5                   10                  15

Glu Val Lys
```

<210> SEQ ID NO 31
<211> LENGTH: 19
<212> TYPE: PRT
<213> ORGANISM: Artificial
<220> FEATURE:
<223> OTHER INFORMATION: CSFV E2 domain mutant vFlc-N2

<400> SEQUENCE: 31

```
Thr Gly Val Ile Glu Cys Thr Asn Val Ser Asn Thr Thr Leu Arg Thr
1               5                   10                  15

Glu Val Lys
```

<210> SEQ ID NO 32
<211> LENGTH: 19
<212> TYPE: PRT
<213> ORGANISM: Artificial
<220> FEATURE:
<223> OTHER INFORMATION: CSFV E2 domain mutant vFlc-N3

<400> SEQUENCE: 32

```
Thr Gly Val Ile Glu Cys Thr Ala Val Ser Asn Thr Thr Asn Arg Thr
1               5                   10                  15

Glu Val Lys
```

<210> SEQ ID NO 33
<211> LENGTH: 19
<212> TYPE: PRT
<213> ORGANISM: Artificial
<220> FEATURE:
<223> OTHER INFORMATION: CSFV E2 domain mutant vFlc-N4

<400> SEQUENCE: 33

```
Thr Gly Val Ile Glu Cys Thr Asn Val Ser Asn Thr Thr Asn Arg Thr
1               5                   10                  15
```

Glu Val Lys

<210> SEQ ID NO 34
<211> LENGTH: 19
<212> TYPE: PRT
<213> ORGANISM: Artificial
<220> FEATURE:
<223> OTHER INFORMATION: CSFV E2 domain mutant vFlc-N5

<400> SEQUENCE: 34

Thr Gly Val Ile Glu Cys Thr Ala Val Ser Asn Asn Thr Leu Arg Thr
1               5                   10                  15

Glu Val Lys

<210> SEQ ID NO 35
<211> LENGTH: 18
<212> TYPE: PRT
<213> ORGANISM: Artificial
<220> FEATURE:
<223> OTHER INFORMATION: CSFV E2 domain mutant vFlc-deltaP

<400> SEQUENCE: 35

Thr Gly Val Ile Glu Cys Thr Ala Val Ser Thr Thr Leu Arg Thr Glu
1               5                   10                  15

Val Lys

<210> SEQ ID NO 36
<211> LENGTH: 17
<212> TYPE: PRT
<213> ORGANISM: Artificial
<220> FEATURE:
<223> OTHER INFORMATION: CSFV E2 domain mutant vFlc-deltaPT

<400> SEQUENCE: 36

Thr Gly Val Ile Glu Cys Thr Ala Val Ser Thr Leu Arg Thr Glu Val
1               5                   10                  15

Lys

<210> SEQ ID NO 37
<211> LENGTH: 17
<212> TYPE: PRT
<213> ORGANISM: Artificial
<220> FEATURE:
<223> OTHER INFORMATION: CSFV E2 domain mutant vFlc-deltaSP

<400> SEQUENCE: 37

Thr Gly Val Ile Glu Cys Thr Ala Val Thr Thr Leu Arg Thr Glu Val
1               5                   10                  15

Lys

<210> SEQ ID NO 38
<211> LENGTH: 16
<212> TYPE: PRT
<213> ORGANISM: Artificial
<220> FEATURE:
<223> OTHER INFORMATION: CSFV E2 domain mutant vFlc-deltaSPT

<400> SEQUENCE: 38

Thr Gly Val Ile Glu Cys Thr Ala Val Thr Leu Arg Thr Glu Val Lys
1               5                   10                  15

<210> SEQ ID NO 39
<211> LENGTH: 16
<212> TYPE: PRT

```
<213> ORGANISM: Artificial
<220> FEATURE:
<223> OTHER INFORMATION: CSFV E2 domain mutant vFlc-deltaVSP

<400> SEQUENCE: 39

Thr Gly Val Ile Glu Cys Thr Ala Thr Thr Leu Arg Thr Glu Val Lys
1               5                   10                  15

<210> SEQ ID NO 40
<211> LENGTH: 15
<212> TYPE: PRT
<213> ORGANISM: Artificial
<220> FEATURE:
<223> OTHER INFORMATION: CSFV E2 domain mutant vFlc-deltaAVSP

<400> SEQUENCE: 40

Thr Gly Val Ile Glu Cys Thr Thr Thr Leu Arg Thr Glu Val Lys
1               5                   10                  15

<210> SEQ ID NO 41
<211> LENGTH: 14
<212> TYPE: PRT
<213> ORGANISM: Artificial
<220> FEATURE:
<223> OTHER INFORMATION: CSFV E2 domain mutant vFlc-deltaSPTTL

<400> SEQUENCE: 41

Thr Gly Val Ile Glu Cys Thr Ala Val Arg Thr Glu Val Lys
1               5                   10

<210> SEQ ID NO 42
<211> LENGTH: 17
<212> TYPE: PRT
<213> ORGANISM: Artificial
<220> FEATURE:
<223> OTHER INFORMATION: CSFV E2 domain mutant vFlc-deltaPTa1

<400> SEQUENCE: 42

Thr Gly Val Ile Glu Cys Thr Ala Gly Ser Thr Leu Arg Thr Glu Val
1               5                   10                  15

Lys

<210> SEQ ID NO 43
<211> LENGTH: 17
<212> TYPE: PRT
<213> ORGANISM: Artificial
<220> FEATURE:
<223> OTHER INFORMATION: CSFV E2 domain mutant vFlc-deltaPTa8

<400> SEQUENCE: 43

Thr Gly Val Ile Glu Cys Thr Ala Glu Ser Thr Leu Arg Thr Glu Val
1               5                   10                  15

Lys

<210> SEQ ID NO 44
<211> LENGTH: 176
<212> TYPE: PRT
<213> ORGANISM: Clastoptera arizonana
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
```

<400> SEQUENCE: 44

Arg Leu Ala Cys Lys Glu Asp Tyr Arg Tyr Ala Ile Ser Ser Thr Asp
1               5                   10                  15

Glu Ile Gly Leu Leu Gly Ala Gly Gly Leu Thr Thr Thr Trp Lys Glu
            20                  25                  30

Tyr Asn His Asp Leu Gln Leu Asn Asp Gly Thr Val Lys Ala Ser Cys
        35                  40                  45

Val Ala Gly Ser Phe Lys Val Thr Ala Leu Asn Val Val Ser Arg Arg
    50                  55                  60

Tyr Leu Ala Ser Leu His Lys Lys Ala Leu Pro Thr Ser Val Thr Phe
65                  70                  75                  80

Glu Leu Leu Phe Asp Gly Thr Asn Pro Ser Thr Glu Glu Met Gly Asp
                85                  90                  95

Asp Phe Arg Ser Gly Leu Cys Pro Phe Asp Thr Ser Pro Val Val Lys
            100                 105                 110

Gly Lys Tyr Asn Thr Thr Leu Leu Asn Gly Ser Ala Phe Tyr Leu Val
        115                 120                 125

Cys Pro Xaa Gly Trp Thr Gly Val Xaa Glu Cys Thr Ala Val Ser Pro
    130                 135                 140

Thr Thr Leu Arg Thr Glu Val Val Lys Thr Phe Arg Arg Asp Lys Pro
145                 150                 155                 160

Phe Pro His Arg Met Asp Cys Val Thr Thr Thr Val Glu Asn Glu Asp
                165                 170                 175

<210> SEQ ID NO 45
<211> LENGTH: 20
<212> TYPE: PRT
<213> ORGANISM: classical swine fever virus

<400> SEQUENCE: 45

Leu Phe Asp Gly Thr Asn Pro Ser Thr Glu Glu Met Gly Asp Asp Phe
1               5                   10                  15

Arg Ser Gly Leu
            20

<210> SEQ ID NO 46
<211> LENGTH: 20
<212> TYPE: PRT
<213> ORGANISM: classical swine fever virus

<400> SEQUENCE: 46

Thr Gly Val Ile Glu Cys Thr Ala Val Ser Pro Thr Thr Leu Arg Thr
1               5                   10                  15

Glu Val Val Lys
            20

<210> SEQ ID NO 47
<211> LENGTH: 12
<212> TYPE: PRT
<213> ORGANISM: classical swine fever virus

<400> SEQUENCE: 47

Tyr Leu Ala Ser Leu His Lys Asp Ala Leu Pro Thr
1               5                   10

<210> SEQ ID NO 48
<211> LENGTH: 9
<212> TYPE: PRT
<213> ORGANISM: classical swine fever virus

```
<400> SEQUENCE: 48

Thr Ala Val Ser Pro Thr Thr Leu Arg
1               5

<210> SEQ ID NO 49
<211> LENGTH: 15
<212> TYPE: PRT
<213> ORGANISM: classical swine fever virus

<400> SEQUENCE: 49

Ile Gly Trp Thr Gly Val Ile Glu Cys Thr Ala Val Ser Pro Thr
1               5                   10                  15

<210> SEQ ID NO 50
<211> LENGTH: 15
<212> TYPE: PRT
<213> ORGANISM: classical swine fever virus

<400> SEQUENCE: 50

Gly Trp Thr Gly Val Ile Glu Cys Thr Ala Val Ser Pro Thr Thr
1               5                   10                  15

<210> SEQ ID NO 51
<211> LENGTH: 15
<212> TYPE: PRT
<213> ORGANISM: classical swine fever virus

<400> SEQUENCE: 51

Trp Thr Gly Val Ile Glu Cys Thr Ala Val Ser Pro Thr Thr Leu
1               5                   10                  15

<210> SEQ ID NO 52
<211> LENGTH: 15
<212> TYPE: PRT
<213> ORGANISM: classical swine fever virus

<400> SEQUENCE: 52

Thr Gly Val Ile Glu Cys Thr Ala Val Ser Pro Thr Thr Leu Arg
1               5                   10                  15

<210> SEQ ID NO 53
<211> LENGTH: 15
<212> TYPE: PRT
<213> ORGANISM: classical swine fever virus

<400> SEQUENCE: 53

Gly Val Ile Glu Cys Thr Ala Val Ser Pro Thr Thr Leu Arg Thr
1               5                   10                  15

<210> SEQ ID NO 54
<211> LENGTH: 15
<212> TYPE: PRT
<213> ORGANISM: classical swine fever virus

<400> SEQUENCE: 54

Val Ile Glu Cys Thr Ala Val Ser Pro Thr Thr Leu Arg Thr Glu
1               5                   10                  15

<210> SEQ ID NO 55
<211> LENGTH: 15
<212> TYPE: PRT
<213> ORGANISM: classical swine fever virus

<400> SEQUENCE: 55
```

-continued

Ile Glu Cys Thr Ala Val Ser Pro Thr Thr Leu Arg Thr Glu Val
1               5                   10                  15

<210> SEQ ID NO 56
<211> LENGTH: 15
<212> TYPE: PRT
<213> ORGANISM: classical swine fever virus

<400> SEQUENCE: 56

Glu Cys Thr Ala Val Ser Pro Thr Thr Leu Arg Thr Glu Val Val
1               5                   10                  15

<210> SEQ ID NO 57
<211> LENGTH: 15
<212> TYPE: PRT
<213> ORGANISM: classical swine fever virus

<400> SEQUENCE: 57

Cys Thr Ala Val Ser Pro Thr Thr Leu Arg Thr Glu Val Val Lys
1               5                   10                  15

<210> SEQ ID NO 58
<211> LENGTH: 15
<212> TYPE: PRT
<213> ORGANISM: classical swine fever virus

<400> SEQUENCE: 58

Thr Ala Val Ser Pro Thr Thr Leu Arg Thr Glu Val Val Lys Thr
1               5                   10                  15

<210> SEQ ID NO 59
<211> LENGTH: 15
<212> TYPE: PRT
<213> ORGANISM: classical swine fever virus

<400> SEQUENCE: 59

Ala Val Ser Pro Thr Thr Leu Arg Thr Glu Val Val Lys Thr Phe
1               5                   10                  15

<210> SEQ ID NO 60
<211> LENGTH: 15
<212> TYPE: PRT
<213> ORGANISM: classical swine fever virus

<400> SEQUENCE: 60

Val Ser Pro Thr Thr Leu Arg Thr Glu Val Val Lys Thr Phe Arg
1               5                   10                  15

<210> SEQ ID NO 61
<211> LENGTH: 15
<212> TYPE: PRT
<213> ORGANISM: classical swine fever virus

<400> SEQUENCE: 61

Ser Pro Thr Thr Leu Arg Thr Glu Val Val Lys Thr Phe Arg Arg
1               5                   10                  15

<210> SEQ ID NO 62
<211> LENGTH: 15
<212> TYPE: PRT
<213> ORGANISM: classical swine fever virus

<400> SEQUENCE: 62

Pro Thr Thr Leu Arg Thr Glu Val Val Lys Thr Phe Arg Arg Glu

```
<210> SEQ ID NO 63
<211> LENGTH: 15
<212> TYPE: PRT
<213> ORGANISM: classical swine fever virus

<400> SEQUENCE: 63

Thr Thr Leu Arg Thr Glu Val Val Lys Thr Phe Arg Arg Glu Lys
1               5                   10                  15

<210> SEQ ID NO 64
<211> LENGTH: 15
<212> TYPE: PRT
<213> ORGANISM: classical swine fever virus

<400> SEQUENCE: 64

Thr Leu Arg Thr Glu Val Val Lys Thr Phe Arg Arg Glu Lys Pro
1               5                   10                  15

<210> SEQ ID NO 65
<211> LENGTH: 176
<212> TYPE: PRT
<213> ORGANISM: classical swine fever virus

<400> SEQUENCE: 65

Arg Leu Ala Cys Lys Glu Asp Tyr Arg Tyr Ala Ile Ser Ser Thr Asp
1               5                   10                  15

Glu Ile Gly Leu Leu Gly Ala Gly Gly Leu Thr Thr Thr Trp Lys Glu
            20                  25                  30

Tyr Asn His Asp Leu Gln Leu Asn Asp Gly Thr Val Lys Ala Ser Cys
        35                  40                  45

Val Ala Gly Ser Phe Lys Val Thr Ala Leu Asn Val Val Ser Arg Arg
    50                  55                  60

Tyr Leu Ala Ser Leu His Lys Lys Ala Leu Pro Thr Ser Val Thr Phe
65                  70                  75                  80

Glu Leu Leu Phe Asp Gly Thr Asn Pro Ser Thr Glu Glu Met Gly Asp
                85                  90                  95

Asp Phe Arg Ser Gly Leu Cys Pro Phe Asp Thr Ser Pro Val Val Lys
            100                 105                 110

Gly Lys Tyr Asn Thr Thr Leu Leu Asn Gly Ser Ala Phe Tyr Leu Val
        115                 120                 125

Cys Pro Ile Gly Trp Thr Gly Val Ile Glu Cys Thr Ala Val Ser Pro
    130                 135                 140

Thr Thr Leu Arg Thr Glu Val Val Lys Thr Phe Arg Arg Asp Lys Pro
145                 150                 155                 160

Phe Pro His Arg Met Asp Cys Val Thr Thr Val Glu Asn Glu Asp
                165                 170                 175
```